(12) United States Patent
Chaganti et al.

(10) Patent No.: US 8,580,713 B2
(45) Date of Patent: *Nov. 12, 2013

(54) TOOL FOR DIAGNOSIS AND PROGNOSIS OF MATURE B-CELL NEOPLASMS

(75) Inventors: Raju S. K. Chaganti, Hillsdale, NJ (US); Jane Houldsworth, Franklin Lakes, NJ (US)

(73) Assignee: Cancer Genetics, Inc., Rutherford, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/475,034

(22) Filed: May 18, 2012

(65) Prior Publication Data

US 2012/0225796 A1 Sep. 6, 2012
US 2013/0130925 A9 May 23, 2013

Related U.S. Application Data

(63) Continuation of application No. 12/980,480, filed on Dec. 29, 2010.

(60) Provisional application No. 61/290,624, filed on Dec. 29, 2009.

(51) Int. Cl.
*C40B 30/04* (2006.01)

(52) U.S. Cl.
USPC .................................................. 506/9

(58) Field of Classification Search
None
See application file for complete search history.

(56) References Cited

FOREIGN PATENT DOCUMENTS

EP 1 829 967 A1 9/2007

OTHER PUBLICATIONS

Wang et al. (Jul. 1, 2004) Bioinformatics vol. 20 pp. 3166 to 3178.*
Pike et al. (Feb. 21, 2008) Leukemia vol. 22 pp. 1035 to 1043.*
Lossos et al. (Aug. 15, 2001) Blood vol. 98 pp. 945 to 951.*
McCarroll, S., et al., "Integrated detection and population-genetic analysis of SNPs and copy numer variation," *Nature Genetics*, Oct. 2008, vol. 40(10), pp. 1166-1174, and Supplementary Information (71 pp.).
Chang, C., et al., "Genomic profiling of plasmablastic lymphoma using array comparative genomic hybridization (aCGH): revealing significant overlapping genomic lesions with diffuse large B-cell lymphoma," *Journal of Hematology & Oncology*, 2009, vol. 2(47), pp. 1-6.
Chen, W., et al., "Array comparative genomic hybridization reveals genomic copy number changes associated with outcome in diffuse large B-cell lymphomas," *Blood*, 2006, vol. 107(6), pp. 2477-2485.
Tagawa, H., et al., "Genome-Wide Array-Based Comparative Genomic Hybridization of Diffuse Large B-Cell Lymphoma: Comparison between CD5-Positive and CD5-Negative Cases," *Cancer Research*, 2004, vol. 64, pp. 5948-5955.
Tagawa, H., et al., "Genome-wide array-based CGH for mantle cell lymphoma: identification of homozygous deletions of the proapoptotic gene BIM," *Oncogene*, 2005, vol. 24, pp. 1348-1358.

* cited by examiner

*Primary Examiner* — Christian Boesen
(74) *Attorney, Agent, or Firm* — Alston & Bird LLP

(57) ABSTRACT

The present invention provides a microarray useful as a tool in the diagnosis and/or prognosis of certain types of cancers, particularly mature B-cell neoplasms. The microarray can include a plurality of genomic regions represented thereon, the genomic regions corresponding to regions wherein alterations, such as copy number alterations, at such locations correlate to specific, identifiable cancers, particularly mature B-cell neoplasms. The invention further provides methods of diagnosing and providing prognosis certain types of cancer, particularly mature B-cell neoplasms. The methods can comprise contacting a sample to a microarray according to the invention, allowing any genetic material in the sample to hybridize to the genomic regions on the microarray, analyzing the hybridizations, and correlating the hybridizations to certain cancer types, particularly mature B-cell neoplasms.

11 Claims, No Drawings

TOOL FOR DIAGNOSIS AND PROGNOSIS OF MATURE B-CELL NEOPLASMS

CROSS-REFERENCE TO RELATED APPLICATIONS

This application is a continuation of U.S. application Ser. No. 12/980,480, filed Dec. 29, 2010, which claims the benefit U.S. application Ser. No. 61/290,624, filed Dec. 29, 2009; both of which are hereby incorporated herein in their entirety by reference.

FIELD OF THE INVENTION

The present invention provides a diagnostic tool useful in the diagnosis and prognosis of cancer, particularly mature B-cell neoplasms. The diagnostic tool can utilize a specific array-comparative genomic hybridization genome scanning technique to detect B-cell malignancies present in a biopsy sample. The invention thus also provides methods for the diagnosis and prognosis of such malignancies, preferentially with minimal invasiveness.

BACKGROUND OF THE INVENTION

Human lymphoid malignancies can be broadly divided into three groups: 1) those arising in B-cells; those arising in T-cells; and those arising in natural killer cells. Within the United States, approximately 85% of lymphoid malignancies are of B-cell origin. During normal B-cell development, after having undergone V(D)J recombination of the immunoglobulin (IG) locus in the bone marrow, immature B-cells move into secondary lymphoid sites, called germinal centers (GC) (Klein U, Dalla-Favera R., "Germinal centres: role in B-cell physiology and malignancy," *Nat Rev Immunol.*, 2008, 8(1): 22-33). Responding to antigenic stimulation, the B-cells passage through the GC, and undergo somatic hypermutation, immunoglobulin class switching, and proliferation, finally being released from the GC either as memory cells or plasmablasts. The latter migrate to the bone marrow and differentiate into long-lived plasma cells. Thus, B-cell malignancies that arise in mature B-cells that have entered the GC share particular genetic features, such as clonal rearrangement and somatic hypermutation of the IGH gene.

Mature B-cell malignancies can include Hodgkin's lymphoma, non-Hodgkin's lymphoma (NHL), and multiple myeloma (MM). Table 1 below provides a listing of lymphoma types and frequencies in the U.S.

TABLE 1

| Group | Subgroup | % of all lymphomas | ~cases dx in 2008 in US |
|---|---|---|---|
| Hodgkin's Lymphoma | | 11% | 8,220 |
| Non-Hodgkin's Lymphoma (NHL): B-cell | Diffuse large B-cell lymphoma (DLBCL) | 28% | 20,600 |
| | Follicular lymphoma (FL) | 20% | 14,550 |
| | Mucosa-associated Lymphatic Tissue (MALT) lymphoma* | 6-7% | 5,610 |
| | Chronic lymphocytic leukemia/small lymphocytic lymphoma (CLL/SLL) | 6% | 4,630 |
| | Mantle cell lymphoma (MCL) | 5% | 3,970 |
| | Mediastinal (thymic) large B-cell lymphoma (MLBL) | 2% | 1,580 |
| | Lymphoplasmacytic lymphoma-Waldenstrom macroglobulinemia | <2% | 1,300 |
| | Nodal marginal zone B-cell lymphoma* | <2% | 1,300 |
| | Splenic marginal zone B-cell lymphoma* | <1% | 650 |
| | Intravascular large B-cell lymphoma | <1% | 650 |
| | Primary effusion lymphoma | <1% | 650 |
| | Burkitt Lymphoma | 2% | 1,650 |
| | Lymphomatoid granulomatosis | <1% | 650 |
| Non Hodgkin's Lymphoma (NHL): T-cell and natural killer cell | | 10% | 8,330 |
| Multiple Myeloma (MM) | | N/A | 19,920 |

*A type of marginal zone lymphoma (MZL)

NHL displays marked heterogeneity recognized at the clinical, pathologic, and genetic levels (2), with the most prevalent being DLBCL, FL, marginal zone lymphomas (MZL, including all three subgroups), CLL/SLL, and MCL. (Good D J, Gascoyne R D., "Classification of non-Hodgkin's lymphoma," *Hematol. Oncol. Clin. North Am."* 2008, 22(5): 781-805, vii.) Overall, mature B-cell neoplasms account for approximately 6% of all cancers in the US, with a male predominance (Jemal A, Siegel R, Ward E, et al. "Cancer statistics, 2008," *CA Cancer J. Clin.,* 2008, 58(2):71-96). NHL is the fifth most prevalent cancer in both males and females. In 2008, the expected number of deaths from these mature B-cell-derived neoplasms was 28,780. Of this number, 4.7% are deaths due to Hodgkin's Lymphoma, 58.2% are due to B-cell NHL, and 37.1% are due to MM.

Diagnosis of mature B-cell neoplasms relies mostly on the pathologic examination of biopsy material (be it either of an incisional or excisional biopsy of a suspect lymph node), a fine needle aspirate of a suspect lymph node (as yet to be considered adequate for initial diagnosis, unless it is the only safe option), or a bone marrow aspirate. Biopsy material is also evaluated for immunophenotype by flow cytometry, for expression of protein markers by immunohistochemistry, for B-cell clonality by IGH rearrangement analysis by PCR, or Southern blotting of genomic DNA, and for the presence of chromosomal abnormalities associated with a specific lymphoma subtype usually by fluorescence in-situ hybridization (FISH) or by PCR. Unlike other cancers, rarely are other biopsy/surgical procedures performed prior to the initiation of treatment, thus limiting the amount of tissue available for diagnostic and prognostic purposes. Few, if any, robust prognostic biomarkers exist for these neoplasms with the exception of CLL/SLL as described herein.

Thus, overall, only few chromosomal/genetic abnormalities are utilized in a clinical laboratory setting to assist in the diagnosis and prognosis of mature B-cell neoplasms. Those were mostly recognized initially through traditional cytogenetic studies and often now are assessed by molecular cytogenetic techniques such as FISH or by molecular genetic techniques such as PCR. Over the years, however, much research effort has been expended in order to identify robust biomarkers of this group of diseases at the DNA, RNA, and protein levels. It was not until genome scanning technologies such as comparative genomic hybridization (CGH) using firstly metaphase chromosomes as hybridization targets and then genome-representative BACs and oligonucleotides as targets, were introduced and became reliable, did the role of genomic gain and loss in lymphoid neoplasms become apparent (Carrasco D R, Tonon G, Huang Y, et al., "High-resolution genomic profiles define distinct clinicopathogenetic subgroups of multiple myeloma patients," *Cancer Cell*, 2006, 9(4):313-25; Chen W, Houldsworth J, Olshen A B, et al., "Array comparative genomic hybridization reveals genomic copy number changes associated with outcome in diffuse large B-cell lymphomas," *Blood*, 2006, 107(6):2477-85; Cheung K J, Shah S P, Steidl C, et al., "Genome-wide profiling of follicular lymphoma by array comparative genomic hybridization reveals prognostically significant DNA copy number imbalances," *Blood*, 2009, 113(1):137-48; Grubor V, Krasnitz A, Troge J E, et al., "Novel genomic alterations and clonal evolution in chronic lymphocytic leukemia revealed by representational oligonucleotide microarray analysis (ROMA)," *Blood*, 2009, 113(6):1294-303; Jardin F, Ruminy P, Kerckaert J P, et al., "Detection of somatic quantitative genetic alterations by multiplex polymerase chain reaction for the prediction of outcome in diffuse large B-cell lymphomas," *Haematologica*, 2008, 93(4):543-50; Kim W S, Honma K, Kaman S, et al., "Genome-wide array-based comparative genomic hybridization of ocular marginal zone B cell lymphoma: comparison with pulmonary and nodal marginal zone B cell lymphoma," *Genes Chromosomes Cancer*, 2007, 46(8):776-83; Largo C, Saez B, Alvarez S, et al., "Multiple myeloma primary cells show a highly rearranged unbalanced genome with amplifications and homozygous deletions irrespective of the presence of immunoglobulin-related chromosome translocations," *Haematologica*, 2007, 92(6):795-802; Lehmann S, Ogawa S, Raynaud S D, et al., "Molecular allelokaryotyping of early-stage, untreated chronic lymphocytic leukemia," *Cancer*, 2008, 112(6):1296-305; Lenz G, Wright G W, Emre N C, et al., "Molecular subtypes of diffuse large B-cell lymphoma arise by distinct genetic pathways," *Proc. Natl. Acad. Sci. U.S.A.*, 2008, 105(36):13520-5; Martinez-Climent J A, Alizadeh A A, Segraves R, et al., "Transformation of follicular lymphoma to diffuse large cell lymphoma is associated with a heterogeneous set of DNA copy number and gene expression alterations," *Blood*, 2003, 101(8):3109-17; Patel A, Kang S H, Lennon P A, et al., "Validation of a targeted DNA microarray for the clinical evaluation of recurrent abnormalities in chronic lymphocytic leukemia," *Am. J. Hematol.*, 2008, 83(7):540-6; Ross C W, Ouillette P D, Saddler C M, Shedden K A, Malek S N, "Comprehensive analysis of copy number and allele status identifies multiple chromosome defects underlying follicular lymphoma pathogenesis," *Clin. Cancer Res.*, 2007, 13(16):4777-85; Rubio-Moscardo F, Climent J, Siebert R, et al., "Mantle-cell lymphoma genotypes identified with CGH to BAC microarrays define a leukemic subgroup of disease and predict patient outcome," *Blood*, 2005, 105(11):4445-54; Sanchez-Izquierdo D, Buchonnet G, Siebert R, et al., "MALT1 is deregulated by both chromosomal translocation and amplification in B-cell non-Hodgkin lymphoma," *Blood*, 2003, 101(11):4539-46; Schraders M, Jares P, Bea S, et al., "Integrated genomic and expression profiling in mantle cell lymphoma: identification of gene-dosage regulated candidate genes," *Br. J. Haematol.*, 2008, 143(2):210-21; Schwaenen C, Nessling M, Wessendorf S, et al., "Automated array-based genomic profiling in chronic lymphocytic leukemia: development of a clinical tool and discovery of recurrent genomic alterations," *Proc. Natl. Acad. Sci. U.S.A.*, 2004, 101(4):1039-44; Schwaenen C, Viardot A, Berger H, et al., "Microarray-based genomic profiling reveals novel genomic aberrations in follicular lymphoma which associate with patient survival and gene expression status," *Genes Chromosomes Cancer*, 2009, 48(1):39-54; Tagawa H, Suguro M, Tsuzuki S, et al., "Comparison of genome profiles for identification of distinct subgroups of diffuse large B-cell lymphoma," *Blood*, 2005, 106(5):1770-7; Takeuchi I, Tagawa H, Tsujikawa A, et al., "The potential of copy number gains and losses, detected by array-based comparative genomic hybridization, for computational differential diagnosis of B-cell lymphomas and genetic regions involved in lymphomagenesis," *Haematologica*, 2009, 94(1): 61-9; Walker B A, Leone P E, Jenner M W, et al., "Integration of global SNP-based mapping and expression arrays reveals key regions, mechanisms, and genes important in the pathogenesis of multiple myeloma," *Blood*, 2006, 108(5):1733-43).

Technologies have evolved for the examination of chromosome abnormalities with differing technical advantages/disadvantages. Examples are shown below in Table 2 (Bejjani B A, Shaffer L G, "Clinical utility of contemporary molecular cytogenetics," *Annu. Rev. Genomics Hum. Genet.*, 2008, 9:71-86).

TABLE 2

Common Technologies for Genomic Aberration Detection

| Technique | Resolution | Coverage | Aberrations Detected |
|---|---|---|---|
| Karyotype | >10 Mbp | Whole genome | Rearrangement (balanced, unbalanced), gain, loss |
| SKY | >2 Mbp | Whole genome | Rearrangement (balanced, unbalanced), gain, loss |
| Chromosomal-CGH | >2 Mbp | Whole genome | Gain, loss |
| FISH | >20 kbp | Probe-specific | Rearrangement (balanced, unbalanced), gain, loss |
| Array-CGH | 5-100 kbp* | Whole genome | Rearrangement (unbalanced), gain, loss |
| SNP-Array | 5 kbp | Whole genome | Gain, loss, uniparental disomy, mutation |
| PCR | <10 kbp | Gene-specific | Rearrangement (balanced, unbalanced), gain, loss, mutation |
| Southern Blotting | <20 kbp | Gene-specific | Rearrangement (balanced, unbalanced), gain, loss |

*5 kbp for oligonucleotide targets, 100 kbp for BAC targets

The above technologies provide limited usefulness and require the following considerations: karyotyping and FISH are labor-intensive; SKY, chromosomal-CGH, FISH, array-CGH, and SNP-array require costly reagents/equipment;

karyotyping requires growth of cells; chromosomal-CGH, array-CGH, SNP-array, PCR, and Southern blotting only require DNA, chromosomal-CGH, array-CGH, and SNP-array require algorithmic analysis; PCR, FISH, and Southern blotting afford the greatest sensitivity. In a clinical diagnostic setting, karyotyping, FISH, PCR, and to a much reduced extent Southern blotting, have been the technologies of choice, and the American College of Medical Genetics (ACMG) has established Standards and Guidelines for these technologies. Standards and Guidelines have been suggested for the performance of array-CGH as a replacement for (or as an adjunct to) standard cytogenetic techniques (e.g., karyotyping, FISH) as commercially available FDA-approved devices, as commercially available Investigational Use Only (IUO) devices requiring validation, or as "home-brew" or in-house developed and validated devices; however, they have not yet been adopted. To date, array-CGH has been utilized primarily as "home-brew" assays.

With increasing resolving power afforded by oligonucleotide arrays, smaller recurrent gains and losses have been identified and common regions of genomic gain/loss have been narrowed. Few alterations have been reported to be associated with the disease or a biologic or clinical feature of the disease. Thus, in mature B-cell neoplasms, the biologic role of genomic gain and loss is still in the discovery phase and the full potential of genomic gain/loss as diagnosticators and prognosticators for the diseases has yet to be explored and exploited in a clinical setting.

SUMMARY OF THE INVENTION

The present invention provides for the assessment of genomic alterations in the diagnosis and prognosis of cancer, particularly mature B-cell neoplasms. In particular, the invention provides the ability to use genome scanning technology, such as array comparative genomic hybridization (array-CGH), as a clinical tool for the diagnosis and prognosis of mature B-cell neoplasms. The invention provides various techniques, platforms, specimen cohort sizes, and treatment modalities that, when used in the mature B-cell neoplasms described herein, can be useful to identify specific types of mature B-cell neoplasm in a sample.

In one aspect, the invention specifically can provide a microarray for detecting the type of mature B-cell neoplasm present in a sample (MatBA). The invention also can provide a microarray for providing a patient prognosis in relation to the presence of mature B-cell neoplasm. In certain embodiments a microarray according to the invention can comprise a substrate with a plurality of distinct genomic regions arrayed thereon. Preferably, each of the distinct genomic regions individually can be capable of hybridizing to material present in the sample. Moreover, the genomic regions arrayed on the substrate can be regions wherein an alteration therein is correlated to one or more types of mature B-cell neoplasm.

In another aspect, the invention also can provide methods of detecting the type of mature B-cell neoplasm present in a sample. The invention also can provide methods of providing a prognosis for a patient having a type of mature B-cell neoplasm. In certain embodiments, a method according to the invention can comprise the following steps: (a) providing a microarray as described herein; (b) providing the sample with labeled genetic material therein; (c) hybridizing the labeled sample genetic material and a labeled reference genetic material with the genomic regions arrayed on the substrate; (d) analyzing the hybridization pattern of the labeled sample genetic material relative to the reference genetic material to the genomic regions to detect the presence of alterations in the sample genetic material; and (e) correlating any detected alterations to the type and outcome of mature B-cell neoplasm associated with the alteration.

DETAILED DESCRIPTION OF THE INVENTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Various technical and scientific terms are used in the present disclosure, and the meaning of said terms is understood to be as expressly defined herein or as otherwise ascertainable from the context of the present disclosure. To the extend such terms are not expressly or inherently defined herein, the meaning of such terms is understood to be the same as commonly understood by one of ordinary skill in the art to which this invention belongs.

As used herein, the term "genomic region" is intended to mean a portion of nucleic acid polymer that is contained within the human genome complement. The term may relate to a specific length of DNA. The term also may be used in relation to specific oligonucleotides. Location of the nucleic acid polymer within the genome can be defined with respect to either the chromosomal band in the human genome or one or more specific nucleotide positions in the human genome.

As used herein, the term "mature B-cell neoplasm" is intended to mean a human lymphoid malignancy arising in B-cells that already have passed into the germinal centers. Mature B-cell malignancies are understood to include Hodgkin's lymphoma, non-Hodgkin's lymphoma (NHL), and multiple myeloma (MM).

The term "Hodgkin's lymphoma" is intended to refer to cancer originating from the lymphocytes and that is characterized by the orderly spread of disease from one lymph node group to another and by the development of systemic symptoms with advanced disease. Diagnosis of Hodgkin's lymphoma is based on the morphologic identification of mononucleated Hodgkin's cells and multinucleated Reed-Sternberg cells and is further subdivided into classical Hodgkin's lymphoma and nodular lymphocyte-predominant Hodgkin's lymphoma (Kuppers R., "The biology of Hodgkin's lymphoma," Nat. Rev. Cancer, 2009, 9(1):15-27). Currently, highly successful treatment involves multi-agent chemotherapy and/or radiotherapy. In this disease, the malignant mature B-cells have lost expression of most B-cell-typical genes and acquired expression of genes associated with other immune cells. Understanding the genetic etiology of such tumors has been challenging due to the scarcity of malignant cells within a specimen and has relied upon microdissection for the isolation of sufficient cells for analysis.

The terms "non-Hodgkin's lymphoma" or "NHL" are intended to refer to the large group of cancers of lymphocytes that do not fall under the classification of Hodgkin's lymphoma. The different types of NHL may be divided into aggressive (fast-growing) and indolent (slow-growing) types, and they can be formed from either B-cells or T-cells. B-cell NHL includes Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, mantle cell lymphoma, marginal zone lymphoma (MZL) (which may be subdivided into mucosa-associated lymphatic tissue (MALT) lymphoma, nodal marginal zone B-cell lymphoma, and splenic marginal zone B-cell lymphoma), mediastinal (thymic) large B-cell lymphoma (MLBL), lymphoplasmacytic lymphoma-Waldenstrom macroglobulinemia, intravascular large B-cell lymphoma, primary effusion lymphoma, and lymphomatoid granulomatosis.

The term "DLBCL" is intended to refer to diffuse large B-cell lymphoma, which is recognized as an aggressive lymphoma. The typical immunophenotype of DLBCL is CD20+, CD45+, and CD3−, where other markers are sometimes used to distinguish it from other lymphoid entities. The incorporation of anti-CD20 immunotherapy (e.g., rituximab) into the chemotherapeutic regimen (CHOP: cyclophosphamide, doxorubicin, vincristine, prednisone) has substantially improved the overall survival of DLBCL patients (Friedberg J W, Taylor M D, Cerhan J R, et al., "Follicular lymphoma in the United States: first report of the national LymphoCare study," *J. Clin. Oncol.* 2009, 27(8):1202-8). Initially, patients are routinely risk-stratified by the International Prognostic Index (IPI) based on age, extranodal involvement, ECOG performance status, stage, and serum LDH levels, which has remained effective in risk-stratification in the rituximab era. For relapsed and refractory patients, second line treatments have also improved with overall approximately two-thirds of DLBCL patients now being cured. Common genetic features variously include 3q26 translocation, 2p16 amplification, 8q24 and 18q21 translocation and amplification, and 17p loss (Chaganti R S, Nanjangud G, Schmidt H, Teruya-Feldstein J., "Recurring chromosomal abnormalities in non-Hodgkin's lymphoma: biologic and clinical significance," *Semin. Hematol.*, 2000, 37(4):396-411). RNA expression profiling studies have identified two subtypes reflecting cells-of-origin (COO) with differing prognosis. Those having an expression signature shared with germinal center B-cells (GCB-DLBCL) generally have a better prognosis than those with an expression signature shared by activated peripheral B-cells (ABC-DLBCL) (Rosenwald A, Wright G, Chan W C, et al., "The use of molecular profiling to predict survival after chemotherapy for diffuse large-B-cell lymphoma," *N. Engl. Med.*, 2002, 346 (25):1937-47). In another study, quantitative estimate of the expression of six genes was found to be sufficient to predict outcome (Lossos I S, Czerwinski D K, Alizadeh A A, et al., "Prediction of survival in diffuse large-B-cell lymphoma based on the expression of six genes," *N. Engl. J. Med.*, 2004, 350(18):1828-37). None of the biomarkers identified to date, are sufficiently robust alone to serve as markers, and none are routinely used in a clinical setting.

The term "FL" is intended to refer to follicular lymphoma, which is an indolent lymphoma with an overall median survival of ten years (Tan D, Horning S J., "Follicular lymphoma: clinical features and treatment," *Hematol. Oncol. Clin. North Am.*, 2008, 22(5):863-82, viii). Diagnosis is generally based on histology though it does have a characteristic immunophenotype: CD 10+, bcl-2+, and bcl-6+. Patients are routinely risk-stratified using the Follicular Lymphoma International Prognostic Index (FLIPI) based on clinical features (age, nodal involvement, hemoglobin level, LDH level, and stage) which continues to have prognostic value in the rituximab era. No single standard of care currently exists in the US for the treatment of de novo FL. Initial therapeutic strategies currently include observation (17.7%), rituximab monotherapy (13.9%), radiation therapy (5.6%), clinical trial (6.1%), chemotherapy alone (3.2%), and chemotherapy plus rituximab (51.9%) with the numbers in parentheses as recently reported by the LymphoCare study cited above. When disease recurs, a biopsy is generally performed to determine if histologic transformation to the more aggressive DLBCL (20-60% of cases) has occurred demanding more aggressive treatment. The t(14;18)(q32;q21) translocation is characteristic of FL where the BCL2 gene is placed under the control of an IGH enhancer. The translocation can be detected by FISH or less comprehensively by PCR (Buchonnet G, Jardin F, Jean N, et al., "Distribution of BCL2 breakpoints in follicular lymphoma and correlation with clinical features: specific subtypes or same disease?" *Leukemia*, 2002, 16(9): 1852-6). RNA expression profiling studies have identified two expression signature patterns associated with outcome highlighting the impact of the microenvironment in this disease: immune response −1 (enriched in T-cell genes, favorable outcome) and −2 (enriched in macrophage and follicular dendritic cell genes, inferior outcome) (Dave S S, Wright G, Tan B, et al., "Prediction of survival in follicular lymphoma based on molecular features of tumor-infiltrating immune cells," *N. Engl. J. Med.*, 2004, 351(21):2159-69). While several biomarkers have been suggested to associate with transformation and outcome, none to date are being routinely used in a clinical setting for risk assessment.

The term "MZL" is intended to refer to marginal zone lymphoma, which is a group of diseases that individually typically are diagnosed by immunophenotyping. The MALT type is the most common and is genetically characterized by four translocations: t(11;18)(q21;q21), t(1;14)(p22;q32), t(14;18)(q32;q21), and t(3;14)(p14;q32) (Zucca E, Bertoni F, Stathis A, Cavalli F., "Marginal zone lymphomas," *Hematol. Oncol. Clin. North Am.*, 2008, 22(5):883-901, viii). For gastric MALT, *Heliobacter pylori* has an important role in the etiology of the disease for which treatment may include antibiotics. FISH for the detection of t(11;18)(q21;q21) is recommended in gastric MALT whose presence is associated with antibiotic resistance (Liu H, Ruskon-Fourmestraux A, Lavergne-Slove A, et al., "Resistance of t(11;18) positive gastric mucosa-associated lymphoid tissue lymphoma to *Helicobacter pylori* eradication therapy," *Lancet*, 2001, 357 (9249):39-40). For *H. pylori*-negative and relapsed MALT and other subgroups of MZL, systemic chemotherapy is indicated with the inclusion of rituximab. While overall MZL is considered an indolent lymphoma, biomarkers of outcome are lacking.

The terms "CLL" and "SLL" are intended to refer to chronic lymphocytic leukemia and small lymphocytic lymphoma, respectively, and may collectively be referred to as CLL/SLL. CLL and SLL are different manifestations of the same disease and are similarly managed. In this disease where some patients have aggressive disease requiring immunochemotherapy (fludarabine, cyclophosphamide, rituximab), and where others will survive for decades without therapy, there have been recent reports of the development of a prognostic index based on both clinical and laboratory features (Shanafelt T D, Jenkins G, Call T G, et al., "Validation of a new prognostic index for patients with chronic lymphocytic leukemia," *Cancer*, 2009, 115(2):363-72; Wierda W G, O'Brien S, Wang X, et al., "Prognostic nomogram and index for overall survival in previously untreated patients with chronic lymphocytic leukemia," *Blood*, 2007, 109(11): 4679-85). With morphologic examination, diagnosis is also based on flow cytometry (kappa/lambda to assess clonality), and the distinguishing immunophenotype is CD5+, CD23+, FMC-7−, and CD20 dim. FISH is recommended for the detection of 11q−, 13q−, +12, and 17p− which have prognostic value, and of t(11;14)(q13;q32) to distinguish CLL/SLL from MCL (Zenz T, Dohner H, Stilgenbauer S., "Genetics and risk-stratified approach to therapy in chronic lymphocytic leukemia," *Best Pract. Res. Clin. Haematol.,* 2007, 20(3):439-53). Mutation status of the variable region of IGH also has prognostic value where unmutated (<2% compared with germline) is associated with aggressive disease (Hamblin T J., "Prognostic markers in chronic lymphocytic leukaemia," *Best Pract. Res. Clin. Haematol.,* 2007, 20(3):455-68). CD38 and ZAP70 expression as assessed by flow cytometry, are considered surrogates for IGH mutation status.

The term "MCL" is intended to refer to mantle cell lymphoma, which is an aggressive lymphoma with a poor long-term prognosis (Schmidt C, Dreyling M., "Therapy of mantle cell lymphoma: current standards and future strategies," *Hematol. Oncol. Clin. North Am.,* 2008, 22(5):953-63, ix). Histologic confirmation is essential either on an excised biopsy or CT-guided core-needle biopsy, with diagnosis determined by morphology and immunohistochemistry with a differential profile of CD5+, CD23−, FMC-7+, and cyclin D1+. These tumors are characterized by the specific t(11;14)(q13;q32) translocation, which juxtaposes the CCND1 gene to the junctional region of IGH, leading to the deregulated expression of cyclin D1. FISH for this translocation can be diagnostic. There is no current standard of care for this disease though conventional cytotoxic chemotherapy such as CHOP has been predominantly utilized with some success with dose-intensified approaches using cytarabine. Many clinical trials are ongoing investigating different treatment modalities including bortezomib (a 26S proteosome inhibitor) and lenalidomide (an immunomodulatory agent) which have exhibited effectiveness in relapsed and refractory MCL (O'Connor O A., "Marked clinical activity of the proteasome inhibitor bortezomib in patients with follicular and mantle-cell lymphoma," *Clin. Lymphoma Myeloma,* 2005, 6(3):191-9). Prognostic biomarkers are in great need for this disease.

The term "MM" is intended to refer to multiple myeloma, which is often preceded by a pre-malignant tumor called monoclonal gammopathy of undetermined significance (MGUS), which occurs in about 3% of individuals over 50 (Kyle R A, Rajkumar S V., "Criteria for diagnosis, staging, risk stratification and response assessment of multiple myeloma," *Leukemia,* 2009, 23(1):3-9; Kyle R A, Rajkumar S V., "Multiple myeloma," *N. Engl. J. Med.,* 2004, 351(18):1860-73). MGUS can progress to MM, the underlying events of which are still unclear. In this essentially incurable disease (overall median survival of 3-5 years), the presence of serum monoclonal immunoglobulin or myeloma protein (M-protein) is diagnostic while the levels of serum beta-2-microglobulin reflect the tumor burden. Karyotyping and FISH have a role in diagnosis and prognosis where translocations involving the IGH (14q32), IGL (22q11), and IGK (2p12) loci are common (Bergsagel P L, Kuehl W M, "Molecular pathogenesis and a consequent classification of multiple myeloma," *J. Clin. Oncol.,* 2005, 3(26):6333-8). For IGH, there are seven recurrent translocation partner sites: 11q13 (CCND1), 12p13 (CCND2), 6p21 (CCND3), 16q23 (MAF), 21q12 (MAFB), 8q24 (MAFA), and 4p16 (MMSET/FGFR3). Low risk disease is associated with t(11;14) and t(6;14), while high risk with t(4;14), t(14;16), and t(14;20) (Stewart A K, Bergsagel P L, Greipp P R, et al., "A practical guide to defining high-risk myeloma for clinical trials, patient counseling and choice of therapy," *Leukemia,* 2007, 21(3):529-34). Secondary genetic events associated with an adverse prognosis include deletions of 17p13 and chromosome 13. In general, patients are risk-stratified according to age and known risk factors. Recently, a guide to defining high risk MM has been reported (mostly based on genetic biomarkers), where identified patients are targeted for clinical trials. Induction treatment in standard risk patients usually involves conventional chemotherapy (vincristine, doxorubicin, and dexamethasone) prior to transplantation, with current data supporting combination with new agents such as bortezomib, thalidomide, and lenalidomide (San-Miguel J, Harousseau J L, Joshua D, Anderson K C, "Individualizing treatment of patients with myeloma in the era of novel agents," *J. Clin. Oncol.,* 2008, 26(16):2761-6).

As used herein, the term "tumor" is intended to mean a neoplastic cell growth and proliferation, whether malignant or benign, as well as pre-cancerous and cancerous cells and tissues.

As used herein, the terms "cancer" and "cancerous" are intended to mean the physiological condition in mammals that is typically characterized by unregulated cell growth. Examples of cancer include, but are not limited to, lymphoma, leukemia, renal cancer, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, carcinoma, melanoma, and brain cancer.

As used herein, the terms "biopsy" and "biopsy specimen" are intended to mean a biological sample of tissue, cells, or liquid taken from the human body.

As used herein, the term "genetic material" is intended to mean materials comprising or formed predominately of nucleic acids. The term specifically is intended to encompass, deoxyribonucleic acids (DNA) or fragments thereof and ribonucleic acids (RNA) or fragments thereof. The term also may be used in reference to genes, chromosomes, and/or oligonucleotides and may encompass any portion of the nuclear genome and/or the mitochondrial genome of the human body.

"Sample genetic material" or "test genetic material" are equivalent terms as used herein which refer to genetic material from a patient, particularly a patient for which an assessment of genomic alterations for the diagnosis and prognosis of cancer, particularly mature B-cell neoplasms is desired. Such sample genetic material or test genetic material may be referred to herein as "sample DNA" or "test DNA" when the genetic material comprises DNA. Furthermore, such sample genetic material or test genetic material can be obtained, for example, from a test sample from the patient described above.

"Reference genetic material" as used herein includes, for example, genetic material from one or more confirmed normal, healthy individuals, particularly one or more individuals that are not known to possess in the genomes one or more of the genomic alterations that are useful for the diagnosis and prognosis of mature B-cell neoplasms as disclosure herein. Such reference genetic material may be referred to herein as reference DNA when the genetic material comprises DNA. Furthermore, such reference genetic material can be obtained, for example, from a reference sample from a normal, healthy individual described above.

As used herein, the term "label" is intended to mean any substance that can be attached to genetic material so that when the genetic material binds to a corresponding site a signal is emitted or the labeled genetic material can be detected by a human observer or an analytical instrument. Labels envisioned by the present invention can include any labels that emit a signal and allow for identification of a component in a sample or reference genetic material. Non-limiting examples of labels encompassed by the present invention include fluorescent moieties, radioactive moieties, chromogenic moieties, and enzymatic moieties.

Chromosome abnormalities are often associated with cancer, and genomic rearrangement, gain/amplification, deletion (loss), uniparental disomy, and mutation are alterations that can affect gene expression (and hence function) effecting multiple disease types, such as developmental syndromes and cancer. The detection and molecular definition of these alterations has stimulated research directed at understanding not only the functional role of the involved gene(s) in disease etiology but also in normal human biology.

Mature B-cell neoplasms arise in B-cells that have entered the germinal center, and they account for approximately 6% of all cancers in the U.S. Diagnosis relies mostly on pathologic examination, immunophenotyping, and detection of only a few genetic markers. The clinical course of these neoplasms ranges from indolent (e.g., FL and MZL) to aggressive (e.g., DLBCL, MCL, and MM). Currently, most risk-stratification for treatment decisions in B-cell neoplasms is based on clinical features, and typical treatment modalities have included chemotherapy, anti-CD20 immunotherapy, proteasomic inhibitors, and immunomodulators. Few prognostic biomarkers are utilized in a clinical setting, and robust biomarkers of diagnosis and of prognosis are in great need.

The present invention provides a tool that is useful in the diagnosis and prognosis of mature B-cell neoplasms. The inventive tool is particularly beneficial because it can be used in new methodologies that utilize minimal available biopsy material, can be carried out with an analyte that is stable, and is less invasive than known procedures for diagnostic/prognostic purposes.

In certain embodiments, the inventive tool can be a microarray for detecting (and thus diagnosing) the type of B-cell neoplasm present in a sample. Particularly, the microarray may employ comparative genomic hybridization (array-CGH) to assist in the diagnosis and prognosis of mature B-cell neoplasms. Comparative genomic hybridization is described, for example, in U.S. Pat. Nos. 5,665,549; 5,721,098 6,159,685; 7,238,484; and 7,537,895; all of which are herein incorporated by reference. Array-CGH is a useful diagnostic tool because it can utilize DNA from fresh, frozen, or formalin-fixed paraffin-embedded (FFPE) specimens and can, in array format, detect genomic gain/loss at a large number of chromosomal loci at one time. The present invention provides a first instance for use of such methods in the area of cancer diagnosis and prognosis.

In particular embodiments, the present invention provides a specific oligonucleotide-based mature B-cell neoplasm array (MatBA) that is useful in diagnosis and prognosis of mature B-cell neoplasms. The MatBA can represent a plurality of distinct genomic regions that exhibit an alteration therein (e.g., gain and/or loss) in mature B-cell neoplasms and can be used in varying techniques, platforms, and statistical algorithms. In specific embodiments, the invention provides technical criteria for alteration detection in available biopsy material. In other embodiments, the invention provides methods wherein mature B-cell neoplasms can be submitted to MatBA array-CGH and alterations correlated to specific types and outcomes of mature B-cell neoplasms. Further, the invention provides a decision tree/model for differential diagnosis and identification of prognostic alterations. Accordingly, the diagnostic tools of the present invention, such as MatBA, are useful in mature B-cell neoplasm diagnosis/prognosis and can be easily integrated into current treatment regimens.

In one aspect, the present invention provides a microarray for detecting the type of mature B-cell neoplasm present in a sample. The microarray specifically may be an oligonucleotide array and can be characterized by the inclusion of genomic regions wherein an alteration in the genomic region is consistent with one or more specific types of mature B-cell neoplasms. More particularly, the genomic regions represented on the microarray may be regions wherein a copy number alteration (CNA) (e.g., gain, loss, or both gain and loss) in the region is consistent with one or more specific types of mature B-cell neoplasms. In other words, the genomic regions included in the inventive microarray may be regions wherein genomic CNAs are shown to be common to specific mature B-cell neoplasms. As more fully described herein, the inventive array thus is useful in the diagnosis and prognosis of mature B-cell neoplasms.

In one embodiment, a microarray according to the invention may comprise a substrate with a plurality of distinct genomic regions arrayed thereon. Any substrate useful in forming diagnostic arrays may be used according to the present invention. For example, glass substrates, such as glass slides, may be used. Other non-limiting examples of useful substrates include silicon-based substrates, metal incorporating substrates (e.g., gold and metal oxides, such as titanium dioxide), gels, and polymeric materials. Useful substrates may be functionalized, such as to provide a specific charge, charge density, or functional group present at the substrate surface for immobilization of materials (e.g., oligonucleotides) to the substrate.

Preferably, each of the distinct genomic regions represented on the inventive microarray is individually capable of hybridizing to material present in a sample (test and/or reference). In certain embodiments, the test sample may comprise all or part of a biopsy or biopsy specimen. In other embodiments, the test sample may comprise tissue that is fresh, frozen, or formalin-fixed paraffin-embedded (FFPE). In further embodiments, the test sample may comprise all or part of a blood or bone marrow specimen, including Ficoll-separated blood/bone marrow mononuclear cells (MNC). In further embodiments, the test sample may comprise all or part of a biopsy specimen, including tissue, core biopsy, or fine needle aspirate. The test sample particularly can comprise genetic material. Preferably, the test sample comprises material in some form capable of hybridizing to the genomic regions represented on the inventive microarray. In specific embodiments, the test sample may comprise DNA or fragments thereof.

Likewise, in certain embodiments, the reference sample may comprise all or part of a biopsy or biopsy specimen from, for example, normal healthy individual. In other embodiments, the reference sample may comprise tissue that is fresh, frozen, or FFPE. In further embodiments, the reference sample may comprise all or part of a blood or bone marrow specimen, including Ficoll-separated blood/bone MNC. In further embodiments, the reference sample may comprise all or part of a biopsy specimen, including tissue, core biopsy, or fine needle aspirate. The reference sample particularly can comprise genetic material. Preferably, the reference sample comprises material in some form capable of hybridizing to the genomic regions represented on the inventive microarray. In specific embodiments, the reference sample may comprise DNA or fragments thereof.

In specific embodiments, the genomic regions arrayed on the substrate can be regions wherein a particular alteration therein is correlated to one or more types of mature B-cell neoplasms. The type of alteration identified can be any alteration, as otherwise described herein, that is correlated to a specific type of mature B-cell neoplasm. In specific embodiments, the alteration can be a copy number alteration, particularly a gain or a loss.

The inventive microarray provides a plurality of genomic regions, and the exact number of genomic regions can vary depending upon the desired use of the microarray (e.g., diagnostic versus prognostic), the desired specificity of the array, and other desired outcomes. Preferably, the microarray comprises a sufficient number of genomic regions to identify a specific type of mature B-cell neoplasm and outcome that may be represented by the test sample. Non-limiting examples of the types of B-cell neoplasms for which identifying genomic regions may be present on the microarray include any type of B-cell non-Hodgkin's lymphoma and multiple myeloma. More specific examples include chronic lymphocytic leukemia/small lymphocytic lymphoma (CLL/SLL), diffuse large B-cell lymphoma, follicular lymphoma, mantle cell lymphoma, and marginal zone lymphoma (MZL) (which may be subdivided into mucosa-associated lymphatic tissue (MALT) lymphoma, nodal marginal zone B-cell lymphoma, and splenic marginal zone B-cell lymphoma). In particular embodiments, a microarray according to the present invention includes a number of genomic regions sufficient to identify the presence in a sample of one or more of diffuse large B-cell lymphoma (DLBCL), follicular lymphoma (FL), marginal zone lymphoma (MZL), chronic lymphocytic leukemia/small lymphocytic lymphoma (CLL/SLL), mantle cell lymphoma (MCL), and multiple myeloma (MM).

The microarray of the invention may comprise only a single genomic region useful to identify a single type of mature B-cell neoplasm (diagnosis) or outcome (prognosis). Preferably, the inventive microarray can comprise a plurality of genomic regions that each can be useful to identify a single type of mature B-cell neoplasm or outcome. As some genomic regions that may be used according to the invention can correlate to two or more different types of mature B-cell neoplasms, it can be useful according to the invention for the microarray to include many different genomic regions having different alterations that correlate to the presence of mature B-cell neoplasms to assist in interpretation of signaling to identify the specific type or types of mature B-cell neoplasms that are identified via the test sample.

The exact number of different genomic regions represented on the inventive microarray can vary based upon the desired outcome of the test in which the array may be used. In specific embodiments, a single microarray according to the invention may comprise at least 2 different genomic regions, at least 5 different genomic regions, at least 10 different genomic regions, at least 15 different genomic regions, at least 20 different genomic regions, at least 25 different genomic regions, at least 30 different genomic regions, at least 35 different genomic regions, at least 40 different genomic regions, at least 45 different genomic regions, at least 50 different genomic regions, at least 55 different genomic regions, at least 60 different genomic regions, at least 65 different genomic regions, at least 70 different genomic regions, at least 75 different genomic regions, or at least 80 different genomic regions. A microarray designed to detect only one or two different types of mature B-cell neoplasms may use a smaller number of different genomic regions, while a microarray designed to detect many different types of mature B-cell neoplasm (e.g., 3, 4, 5, 6, or even more) could include a much larger number of different genomic regions. Further, each different genomic region can be included in the array in multiple copies. The total number of genomic regions provided on a single microarray according to the invention thus can be greater than about 100, greater than about 250, greater than about 500, greater than about 1,000, greater than about 2,500, greater than about 5,000, greater than about 10,000, greater than about 15,000, greater than about 20,000, greater than about 25,000, greater than about 30,000, greater than about 35,000, greater than about 40,000, greater than about 45,000, or greater than about 50,000. In certain embodiments, the total number of genomic regions provided on a single microarray can be at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or more different genomic regions.

In certain other embodiments, the genomic regions used on the inventive microarray may be identified in relation to chromosomal bands (although the region represented on the array need not necessarily include the entire band). Particularly, the plurality of genomic regions may comprise at least one chromosomal band selected from the group shown in Table 3 provided herein. In addition to varying based upon the different regions that may be represented on the microarray, the device of the present invention also may vary based upon probe density within specific regions and multiplicity of arrayed oligonucleotides.

As evident from above, the inventive microarray can be designed to incorporate genomic regions wherein a specific alteration, such as a gain or loss, correlates genetic material hybridized (e.g., DNA or fragments thereof) therewith to a specific type of mature B-cell neoplasm or overall prognosis of the respective patient. Because of the identification of a large number of different genomic regions that correlate to a large number of different types of mature B-cell neoplasm and their respective clinical outcomes, it is possible according to the invention to provide a single array (e.g., a single chip or a single slide) to which a test sample can be applied and identify whether one or more of the specific types of mature B-cell neoplasm represented in the array is actually present in the test sample (and thus would be present in the source from where the test sample was derived—e.g., a tumor biopsy) and the prognosis of the patient from which the biopsy was derived. Thus, the inventive microarray can provide a clear diagnostic and prognostic purpose.

In addition to the genomic regions described above that are present on the substrate, the inventive microarray also may comprise one or more probes that may be useful for normalization of test results or to use as a comparative for analytical purposes. For example, in one embodiment, a "backbone" probe set may be used that covers the entire chromosomal complement. Such backbone probe set may comprise varying numbers of probes at varying levels of resolution and preferably excludes regions of known copy number variation.

The inventive array also may be used to provide a prognostic purpose. For example, the inventive array could be designed to identify the cell-of-origin subtype in a specific type of mature B-cell neoplasm. Specifically, the array could be designed to identify whether diffuse large B-cell lymphoma is germinal center B-cell type (GCB) DLBCL or activated B-cell type (ABC) DLBCL. Likewise, the array can be used to identify transformation in follicular lymphoma and/or designed to estimate overall survival in all types of mature B-cell neoplasms.

In a further aspect, the present invention provides methods for detecting the type of mature B-cell neoplasm present in a sample. Table 4 shown below in the Experimental section shows correlations between specific CNAs at specific genomic regions and six types of mature B-cell neoplasms including outcome. A person skilled in the art using the present disclosure would be able to identify even further correlations between alterations at specific genomic regions and further types of cancers and thus could apply the presently described methods and devices in even further applications. Such further applications are intended to be encompassed by the present invention.

In one embodiment, a method for detecting the type of mature B-cell neoplasm present in a sample may comprise providing a microarray as otherwise described herein. As noted above, the present invention encompasses a number of different variations of microarrays and all such microarrays could be used in the inventive methods. Preferably, the microarray used in the method comprises genomic regions wherein alterations in such regions correlate to the type and outcome of mature B-cell neoplasms being tested for or which are anticipated likely to be present in the sample being tested.

In further embodiments, the inventive methods may comprise providing the sample with labeled genetic material therein. In carrying out the method of the invention, a sample for testing may be provided in a form wherein any genetic material present in the test sample already has been subjected to a labeling procedure to provide labels suitable for use according to the invention. In other embodiments, the method may comprise the actual step of labeling the genetic material present in the sample. Any method suitable for labeling of genetic material, such as DNA, may be used according to the invention. For example, the DNA could be digested with a suitable material, such as Rsa I and/or Alu I, and then appropriately labeled. In one embodiment, fluorescent labeling may be used (such as, for example, Cyanine 5-dUTP (Cy5) or Cyanine 3-dUTP (Cy3) using Klenow DNA polymerase).

In addition to the labeled test genetic material (i.e., the genetic material in the sample taken from a biopsy to be tested), labeled reference genetic material is used. Such reference genetic material can include, for example, genetic material from confirmed normal healthy individuals.

The method of the invention further may comprise hybridizing the labeled genetic materials (test and reference) with the genomic regions arrayed on the substrate. Any hybridization method useful in the art could be used in hybridizing the genetic materials with the genomic regions. One method could encompass combining the labeled genetic materials (test and reference), human Cot-1, a blocking agent, and a hybridization buffer, and allowing the labeled genetic materials to hybridize with the genomic regions on the microarray for a sufficient time (e.g., about 24 hours) under acceptable conditions (e.g., a temperature of about 65° C.). Hybridization kits and techniques commercially available, such as from Agilent Technologies, could be used.

The inventive methods further can comprise analyzing the hybridization pattern of the labeled genetic materials to the genomic regions. Such is useful to detect the presence of alterations in the genetic material from the sample relative to the reference genetic material. Analyzing methods useful according to the present invention can vary depending upon the type of labeling used. Preferably, analyzing can be carried out using equipment useful to evaluate hybridization patterns and identify regions on the microarray where alterations in the test sample occur.

In certain embodiments of the invention, the methods of the involve providing a microarray comprising a substrate with a plurality of distinct genomic regions arrayed thereon, wherein each of the distinct genomic regions is individually capable of hybridizing to material present in said sample, and wherein the genomic regions arrayed on the substrate are regions wherein an alteration therein is correlated to one or more types of mature B-cell neoplasm. The methods further involve providing a sample with labeled sample genetic material therein and also provided labeled reference genetic material. Typically, the sample is from a patient, particularly a patient for which an assessment of genomic alterations for the diagnosis and prognosis of cancer, particularly mature B-cell neoplasms is desired. The methods further in comprising hybridizing the labeled sample genetic material and the labeled reference genetic material with the genomic regions arrayed on the substrate. In a preferred embodiment of the invention, the labeled sample genetic material comprises a first label and the labeled reference genetic material comprises a second label, wherein the labels wherein the first and second labels are non-identical and can be detected simultaneously when hybridized to at least one genomic region on the substrate. Preferably, the labeled sample genetic material and the labeled reference material are hybridized with the genomic regions arrayed on the substrate at the same time. The methods of the invention further involve analyzing the hybridization pattern of the labeled sample genetic material and the labeled reference genetic material to the genomic regions to detect the presence of alterations in the genetic material from the sample and can further involve correlating any detected alterations to the type of mature B-cell neoplasm associated with the alteration.

In certain embodiments, the methods of the invention analyzing the hybridization pattern can involve imaging a microarray such as, for example, the imaging methods described in U.S. Pat. No. 7,636,636; herein incorporated by reference. Such methods can involve, for example, acquiring an image of a microarray including a target spot; processing the image to correct for background noise and chip misalignment; analyzing the image to detect target spots; analyzing the image to identify the target patch, editing debris and correcting for ratio bias; detecting number variation in the target spot by an objective statistical analysis, wherein the sample genetic material and the reference genetic material form the target spot by the hybridizing; measuring a fluorescent signal intensity of the target spot from the sample genetic material and the reference genetic material; obtaining an image; and cross-correlating the image to the image of the microarray. Such imaging methods typically the use of computer programs for analyzing the imaged microarrays. See e.g., U.S. Pat. No. 7,636,636.

The inventive methods also can include correlating any detected alterations to the type and outcome of mature B-cell neoplasm associated with the alteration. Table 4 provided herein exemplifies several correlations of alterations at specific genomic regions to six types of mature B-cell neoplasms. Table 5 exemplifies a specific test where CNAs were evaluated in a specific tumor and illustrates the ability to detect alterations at the specifically disclosed genomic regions and correlate the detected alterations to specific types and outcomes of mature B-cell neoplasms.

EXAMPLE 1

Development of a Microarray for Diagnosis and Prognosis of Mature B-cell Neoplasms A study was performed to facilitate development of tools (particularly the microarray—e.g., the MatBA—described herein) for the use in the diagnosis and prognosis of mature B-cell neoplasms. Initially, an evaluation was performed of molecular cytogenetic and molecular genetic applications in the study of mature B-cell neoplasms. These studies utilized chromosomal CGH, FISH, array CGH (BAC and oligonucleotide), SNP-array, ROMA, and/or PCR-based assessment of single gene copy numbers. For each subtype to be assessed in the MatBA, genomic regions with copy number alterations (CNA) were identified in at least two reports occurring in at least 5% of specimens in each report. A panel of genomic regions was then selected to be represented on the MatBA, whose respective gain and/or loss is frequent for each subtype and has the potential to assist in prognosis. Regions were also targeted to contain those reported to be associated with a disease feature that may have prognostic value. Table 3 lists the regions used in one embodiment of a microarray according to the present invention, the regions being identified according to cytogenetic band and physical location within the chromosome, according to the hg18 assembly (http://genome.ucsc.edu/).

TABLE 3

Genomic Regions Represented on MatBA

| Band* | Location | Size (Mbp) |
|---|---|---|
| 1p36.32-p36.23 | chr1: 1.5-9.4 | 7.9 |
| 1p21 | chr1: 94.0-107 | 13 |
| 1p13.2-p13.1 | chr1: 111.6-117.6 | 6 |
| 1q21 | chr1: 142.4-153.3 | 10.9 |
| 1q31 | chr1: 184.6-204.3 | 19.7 |
| 1q41-q44 | chr1: 236.5-244.5 | 8 |
| 2p25.3 | chr2: 2.4-4.1 | 1.7 |
| 2p16.1-p15 | chr2: 59.3-63.9 | 4.6 |
| 2p11.2-q11.2 | chr2: 88-90 | 2 |
| 2q13-q14.1 | chr2: 113.6-114.2 | 0.6 |
| 2q24 | chr2: 154.6-169.5 | 14.9 |
| 3p22 | chr3: 32.1-42 | 9.9 |
| 3p14.1-p13 | chr3: 69.9-73.7 | 3.8 |
| 3q12.2-q12.3 | chr3: 102.0-103.2 | 1.2 |
| 3q21.2 | chr3: 126.4-126.7 | 0.3 |
| 3q22 | chr3: 131.5-140.4 | 8.9 |
| 3q26.1-q26.2 | chr3: 161.2-172.5 | 11.3 |
| 3q26.31 | chr3: 173-175 | 2 |
| 3q27 | chr3: 184.2-189.4 | 5.2 |
| 4p15 | chr4: 24.9-34.7 | 9.8 |
| 4q11-q12 | chr4: 52-56 | 4 |
| 4q24 | chr4: 102-104.8 | 2.8 |
| 4q34.3-q35 | chr4: 178.3-189.9 | 11.6 |
| 5p15 | chr5: 0-10 | 10 |
| 5q13.2-q13.3 | chr5: 73-76 | 3 |
| 5q31.3 | chr5: 140-141 | 1 |
| 6p25 | chr6: 0-7 | 7 |
| 6p21.31-p21.2 | chr6: 35.7-37.7 | 2 |
| 6p21.1 | chr6: 41-43 | 2 |
| 6q12 | chr6: 66.9-67.2 | 0.3 |
| 6q16 | chr6: 92-104.8 | 12.8 |
| 6q21 | chr6: 108-110.5 | 2.5 |
| 6q22 | chr6: 113.9-130.4 | 16.5 |
| 6q23.3-q24 | chr6: 137.2-149.1 | 11.9 |
| 6q25 | chr6: 152.2-153.2 | 1 |
| 7p22 | chr7: 0-7.2 | 7.2 |
| 7p21.3-p21.2 | chr7: 12.9-14.6 | 1.7 |
| 7q31 | chr7: 107.2-126.9 | 19.7 |
| 8p23 | chr8: 0-12.7 | 12.7 |
| 8p21.3 | chr8: 18.7-23.2 | 4.5 |
| 8p12-p11.23 | chr8: 37.4-39.4 | 2 |
| 8q21.2 | chr8: 86.6-86.9 | 0.3 |
| 8q24.21 | chr8: 127.3-131.5 | 4.2 |
| 9p24.2-p24.1 | chr9: 4.0-6.0 | 2 |
| 9p21 | chr9: 19.9-32.8 | 12.9 |
| 9q22 | chr9: 89.6-101.6 | 12 |
| 9q33.2-q34.1 | chr9: 122-132 | 10 |
| 10p14 | chr10: 6.7-12.3 | 5.6 |
| 10p12.31-p12.2 | chr10: 21.6-24.1 | 2.5 |
| 10q23.2 | chr10: 87.9-89.8 | 1.9 |
| 11p13 | chr11: 33.0-34.5 | 1.5 |

TABLE 3-continued

Genomic Regions Represented on MatBA

| Band* | Location | Size (Mbp) |
|---|---|---|
| 11q13 | chr11: 63.1-76.7 | 13.6 |
| 11q22.1-q22.2 | chr11: 100.8-102.2 | 1.4 |
| 11q22.3-q23 | chr11: 106.7-120.7 | 14 |
| 11q25 | chr11: 132.5-134.5 | 2 |
| 12p13.1 | chr12: 12.6-14.8 | 2.2 |
| 12q13.1-q13.2 | chr12: 44.6-56.5 | 11.9 |
| 12q15 | chr12: 66-69.8 | 3.8 |
| 13q14 | chr13: 39.5-52.2 | 12.7 |
| 13q31 | chr13: 77.8-93.8 | 16 |
| 13q33-q34 | chr13: 100.5-114.1 | 13.6 |
| 14q12 | chr14: 23.5-32.5 | 9 |
| 14q32 | chr14: 90.1-105.1 | 15 |
| 15q21.1 | chr15: 44.0-45.5 | 1.5 |
| 15q23-q24 | chr15: 65-75 | 10 |
| 16p13.3 | chr16: 0-6.3 | 6.3 |
| 16p13.13 | chr16: 10.3-12.3 | 2 |
| 16p11.1-p11.2 | chr16: 27.6-38.2 | 10.6 |
| 16q24 | chr16: 83.6-88.8 | 5.2 |
| 17p13 | chr17: 0-11.2 | 11.2 |
| 17q22-q23.1 | chr17: 53-55 | 2 |
| 17q24.2-q25.1 | chr17: 64.1-69.9 | 5.8 |
| 18p11 | chr18: 0-16.1 | 16.1 |
| 18q21 | chr18: 41.8-59.8 | 18 |
| 18q23 | chr18: 75.1-75.4 | 0.3 |
| 19p13.3-p13.2 | chr19: 0.2-11.2 | 11 |
| 19q13.33-q13.43 | chr19: 53.8-63.8 | 10 |
| 20q13 | chr20: 41.1-62.4 | 21.3 |
| 21q21 | chr21: 15.3-30.5 | 15.2 |
| 22q12 | chr22: 20-35.9 | 15.9 |

*The region represented on the array does not necessarily include the entire band.

Table 4 lists the genomic regions represented on the microarray and the expected alteration for each region and correlates this information to each type of mature B-cell neoplasm identifiable according to this embodiment of the array. Also shown in Table 4 are the alterations associated mostly with a clinical feature or a biologic feature. Thus, in specific embodiments, the MatBA can comprehensively represents 606 Mbp (approximately one-fifth of the human genome), targeting regions that are commonly gained/lost in mature B-cell neoplasms.

TABLE 4

Genomic regions represented on MatBA and respective alteration (gain [G] or loss [L]) in each subtype

| Band | DLBCL | FL | MZL | CLL/SLL | MCL | MM |
|---|---|---|---|---|---|---|
| 1p36.32-p36.23 | L*§ | L¶† | G | | | G |
| 1p21 | L | | | | L | G/L |
| 1p13.2-p13.1 | L | | | | | G/L |
| 1q21 | G | G | G | | | G |
| 1q31 | G§ | G¶ | G | | | |
| 1q41-q44 | G | | G¶ | | | G |
| 2p25.3 | G/L¶ | G | | G | | |
| 2p16.1-p15 | G§ | G | | G | | |
| 2p11.2-q11.2 | G/L | G | | | L | |
| 2q13-q14.1 | L | G | | | | |
| 2q24 | L | G | | | | |
| 3p22 | G‡¶/L | | G | | | G |
| 3p14.1-p13 | G‡¶/L | | G | | | G |
| 3q12.2-q12.3 | G‡¶ | | G | | G | G |
| 3q21.2 | G‡¶ | | | | G¶ | G |

TABLE 4-continued

Genomic regions represented on MatBA and respective alteration (gain [G] or loss [L]) in each subtype

| Band | DLBCL | FL | MZL | CLL/SLL | MCL | MM |
|---|---|---|---|---|---|---|
| 3q22 | G‡¶ | | G | | G¶ | G |
| 3q26.1-q26.2 | G‡¶ | | G | | G¶ | G |
| 3q26.31 | G‡¶ | | G | | G¶ | G |
| 3q27 | G‡¶ | G† | G | | G¶ | G |
| 4p15 | L | G† | | | | |
| 4q11-q12 | L | | | | | |
| 4q24 | L | | | | | G |
| 4q34.3-q35 | L | | | | | |
| 5p15 | G | G | | | | G |
| 5q13.2-q13.3 | | | | | | G |
| 5q31.3 | G | | | | | G |
| 6p25 | G | G† | | | | G |
| 6p21.31-p21.2 | G | G† | G | | | G |
| 6p21.1 | G | G† | | | | G |
| 6q12 | L‡€ | L¶ | | | L | G/L |
| 6q16 | L‡¶ | L†¶ | | | L | G/L |
| 6q21 | L‡¶ | L†¶ | | | L | G/L |
| 6q22 | L‡¶ | L†¶ | | | L | G/L |
| 6q23.3-q24 | L‡¶ | L†¶ | L | | L | G/L |
| 6q25 | L‡¶ | L¶ | | | L | G/L |
| 7p22 | G | G†¶ | | | G | |
| 7p21.3-p21.2 | G/L | G†¶ | | | G | |
| 7q31 | G§ | G† | | L | | |
| 8p23 | L | G/L† | | L | L | L |
| 8p21.3 | L | | | | L¶ | L |
| 8p12-p11.23 | | | | | | L |
| 8q21.2 | G | G¶ | | | G | |
| 8q24.21 | G§ | G | | G | G | G |
| 9p24.2-p24.1 | G€ | | | | L¶ | G |
| 9p21 | G€/L‡¶ | L¶ | | | L¶ | G |
| 9q22 | G€§ | | | | L¶ | G |
| 9q33.2-q34.1 | G€‡ | | G | | | G |
| 10p14 | L€ | | | | L | |
| 10p12.31-p12.2 | L€ | | | | | G |
| 10q23.2 | L€§ | L | | | | |
| 11p13 | G | | | | | G |
| 11q13 | G | G | G | | G/L | G |
| 11q22.1-q22.2 | G | G¶ | | | L | G/L |
| 11q22.3-q23 | G | G¶ | | L | L | G/L |
| 11q25 | G/L§ | G¶ | | | L | L |
| 12p13.1 | G¶§ | G | | G | | L |
| 12q13.1-q13.2 | G§ | G† | G | G | G | L |
| 12q15 | G§ | G† | G | G | G | L |
| 13q14 | G/L§ | L† | | L | L¶ | L |
| 13q31 | G¶§/L | G/L† | | | G/L | L |
| 13q33-q34 | G¶/L§ | G/L† | L | | L¶ | L |
| 14q12 | | | | | | L |
| 14q32 | L | | | | | L |
| 15q21.1 | L | | | | | G |
| 15q23-q24 | G¶/L | G | | | | G |
| 16p13.3 | G | G | | | | L |
| 16p13.13 | G‡ | G | | | | L |
| 16p11.1-p11.2 | G/L¶ | G | | | | L |
| 16q24 | L | G | | | | L |
| 17p13 | G/L¶ | L¶ | L¶ | L¶ | L¶ | G/L |
| 17q22-q23.1 | G | G¶ | | | | G |
| 17q24.2-q25.1 | G | G¶ | | | | G |
| 18p11 | G | G | G | | | G |
| 18q21 | G‡¶ | G¶ | G | | G | G |
| 18q23 | G‡¶ | G¶ | G | | | G |
| 19p13.3-p13.2 | G | L | | | | G |
| 19q13.33-q13.43 | G/L‡ | | | | | G |
| 20q13 | G | | G | | | L |
| 21q21 | G | G | | | | G |
| 22q12 | G | L | | L | L | L |

*Only those alterations occurring at frequencies higher than at least 5% in at least two studies are listed.
¶Associated with overall survival,
‡Associated with ABC COO expression signature,
§Associated with GCB COO expression signature,
†Associated with transformation,
€ Associated with primary mediastinal B-cell lymphoma In one embodiment, the overall format of the oligonucleotide array was designed taking into account the following considerations: documented genomic regions of gain/loss, duplicity of probes on the array, resolution of probes for documented gain/loss, ease of performance of array hybridization, ease of analysis of data for a clinical laboratory, and economic viability as discussed below. Oligonucleotide arrays were designed through eARRAY (Agilent Technologies) utilizing the library of probes within eARRAY that map to the respective regions including probes that map to both exons and introns. Also included in the array design was a "backbone" probe set of approximately 3,100 probes (provided by Agilent) that cover the entire chromosomal complement at a resolution of approximately 1 Mbp excluding regions of known CNV. The MatBA was designed in the 4×44,000 (4×44K) format allowing the hybridization of four independent samples to each slide.

In general, DNAs were labeled and hybridized to the arrays on glass slides essentially as recommended by the manufacturer. Specifically, 1 μg of each test and reference DNAs were digested with Rsa I and Alu I and then differentially labeled with Cyanine 5-dUTP (Cy5) or Cyanine 3-dUTP (Cy3) using Klenow. Following removal of unincorporated nucleotides, the amounts of DNA and specific activities were determined. Prior to hybridization, equal amounts of the test and reference DNAs were mixed (range of 1.5-3.0 μg each), together with human Cot-1, a blocking agent, and hybridization mix.

The glass slide substrate (containing 4 arrays) was hybridized for 24 hours at 65° C. and then washed according to the manufacturer's recommendations with the inclusion of a wash in acetonitrile and a stabilizing and drying agent to minimize the ozone-induced degradation of the fluorophores, in particular Cy5. The slides were scanned using an Agilent scanner providing a scanned image (.tif) from which data were extracted using Feature Extraction (Agilent) (using the entire array unless otherwise stated). This software also provides data reporting the quality of hybridization (QC Metrics). Data are then further analyzed in DNA Analytics (Agilent) for aberration detection, using the ADM2 statistical package. Regions less than 250 kbp showing gain/loss were excluded due to consistent mapping to known CNV locations according to the Database of Genomic Variants (available at http://projects.tcag.ca/variation/; Iafrate et al. (2004) Nat. Genet. 36:949-51) and to the observation that such gain and loss was very often common to multiple specimens at low significance.

The ability of the MatBA to confirm previously identified CNAs was assessed using DNAs from ten lymphoma/leukemia cell lines whose genomic copy number profiles were determined using SNP6-arrays (Affymetrix, comprising 946K copy number probes) and are publicly available (available on the world-wide web at: www.sanger.ac.uk/cgi-bin/genetics/CGP/cghviewer/CghHome.cgi). The results expected and those obtained for the ten cell lines are provided in Table 5.

TABLE 5

Expected and obtained genomic gains and losses for ten leukemia/lymphoma cell lines using MatBA (v4)

| | 697 (2) | | EB2 (4) | | L-428 (4) | | Daudi (4) | | Raji (4) | | HDLM-2 (2) | | KM-H2 (3) | | SK-MM-2 (2) | | RPMI-8402 (4) | | HT (2) | |
|---|---|---|---|---|---|---|---|---|---|---|---|---|---|---|---|---|---|---|---|---|
| # | E | O | E | O | E | O | E | O | E | O | E | O | E | O | E | O | E | O | E | O |
| 1 | | | | • | | • | | • | ■ | ■ | • | • | ■ | ■ | | • | ■ | | | |
| 2 | | | | ■ | ■ | ■ | | • | | • | | • | • | • | • | • | | | | |
| 3 | | | | | ■ | ■ | | | | • | | ■ | ■ | ■ | | | | | | |
| 4 | • | | | • | • | • | | • | • | • | | • | • | • | | • | | | | • |
| 5 | ■ | ■ | | • | | • | | • | | • | | • | ■ | ■ | | • | | | | • |
| 6 | ■ | ■ | | • | | | | | | • | | | ■ | ■ | | | | | | • |
| 7 | | | | • | • | | | | | • | | | ■ | ■ | • | | | | ■ | ■ |
| 8 | | | | | ■ | ■ | | | | • | ■ | ■ | ■ | ■ | | | | | ■ | ■ |
| 9 | ■ | | ■ | • | ■ | • | ■ | ■ | ■ | | ■ | ■ | ■ | ■ | | ■ | ■ | • | | |
| 10 | | | | | ■ | ■ | | | | | | ■ | | | | | | | ■ | ■ |
| 11 | | • | | • | ■ | • | | • | | • | | • | ■ | ■ | | • | • | • | • | • |
| 12 | | | | • | | | | | | • | | • | • | • | | | • | | | |
| 13 | | | | | | | | | • | • | | • | • | • | | • | • | | | |
| 14 | | | | | | | | ■ | | | ■ | | ■ | ■ | | | | | | |
| 15 | | | | • | | | | ■ | | | ■ | ■ | ■ | ■ | | | | | | |
| 16 | • | | | • | • | | | ■ | | • | | | | • | | | | | | |
| 17 | | | | • | • | | • | ■ | | • | ■ | • | ■ | | | • | • | | | |
| 18 | | | | • | • | • | | ■ | | • | ■ | ■ | ■ | ■ | | | ■ | | | |
| 19 | | | | | | | | ■ | | • | ■ | ■ | ■ | ■ | | | • | | | |
| 20 | | | ■ | ■ | | ■ | | ■ | | • | | ■ | • | • | • | • | | | ■ | ■ |
| 21 | | | ■ | ■ | | ■ | | | | | ■ | ■ | | • | | | | | | |
| 22 | | | ■ | ■ | | ■ | | | | • | | ■ | ■ | ■ | | | ■ | | | |
| 23 | | | ■ | ■ | | ■ | | • | | • | | • | ■ | ■ | | | | | | |
| 24 | | | ■ | • | • | ■ | | • | | • | ■ | ■ | ■ | ■ | | | | | | |
| 25 | | | | | ■ | ■ | | | | | | ■ | | • | | • | • | | | |
| 26 | | | | | | | | | | | | | ■ | ■ | | | ■ | | | |
| 27 | | | ■ | ■ | | • | | | | | | • | ■ | ■ | | | | | | |
| 28 | | | | ■ | | | | | | | | • | ■ | ■ | | • | | | | |
| 29 | | | | ■ | | | | | | • | | | ■ | ■ | | | | | | |
| 30 | | | ■ | ■ | ■ | ■ | | | | ■ | | | ■ | ■ | | | | | | |
| 31 | ■ | • | ■ | ■ | ■ | ■ | • | | • | ■ | | • | ■ | ■ | ■ | ■ | ■ | | | |
| 32 | ■ | | ■ | ■ | ■ | ■ | | | | ■ | | ■ | ■ | ■ | ■ | ■ | | | | |
| 33 | ■ | | ■ | ■ | ■ | ■ | | • | | ■ | | • | ■ | ■ | ■ | ■ | | | | • |
| 34 | | | ■ | ■ | ■ | ■ | | • | | ■ | • | ■ | ■ | ■ | ■ | ■ | | • | | |
| 35 | | | ■ | ■ | | | | | | ■ | | | ■ | ■ | ■ | ■ | | | | |
| 36 | | | | ■ | ■ | ■ | | • | | ■ | ■ | • | ■ | ■ | | | • | | | |
| 37 | | | | | ■ | • | | ■ | | ■ | ■ | ■ | ■ | ■ | | | ■ | | | |
| 38 | | | • | ■ | ■ | ■ | | • | | • | | • | ■ | ■ | | | ■ | | | |
| 39 | | | ■ | ■ | ■ | • | | • | ■ | ■ | ■ | ■ | ■ | ■ | ■ | ■ | • | | | |
| 40 | | | ■ | ■ | ■ | ■ | | | ■ | ■ | ■ | ■ | ■ | ■ | ■ | ■ | | | | |
| 41 | | | ■ | ■ | ■ | ■ | | | ■ | ■ | ■ | ■ | ■ | ■ | ■ | ■ | • | | | |
| 42 | ■ | ■ | ■ | ■ | ■ | | | | ■ | ■ | | | ■ | ■ | ■ | ■ | | | | |
| 43 | ■ | ■ | • | ■ | ■ | ■ | | | | • | ■ | • | • | | ■ | ■ | | | | |
| 44 | | | ■ | ■ | ■ | ■ | | • | | • | ■ | ■ | ■ | ■ | ■ | ■ | | | | |
| 45 | | | • | ■ | ■ | ■ | | • | | • | ■ | • | ■ | ■ | ■ | ■ | | | | |
| 46 | | | | ■ | ■ | ■ | | | | • | | • | | • | | | | | | |
| 47 | | | | ■ | ■ | ■ | | | | • | | ■ | ■ | • | | • | | | | |
| 48 | | | ■ | • | | • | | | | • | | • | ■ | ■ | | | | | | |
| 49 | | | ■ | • | | | | | | | | • | | | | | • | | | |
| 50 | | | ■ | | | | | | | | | | ■ | ■ | | | | | | |
| 51 | | | | | | | | | | | | • | • | | | | | | | |

TABLE 5-continued

Expected and obtained genomic gains and losses for ten leukemia/lymphoma cell lines using MatBA (v4)

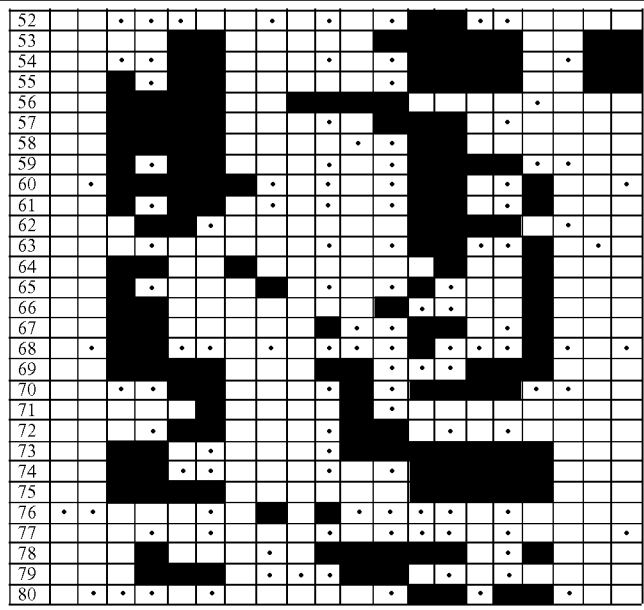

E = expected,
O = observed,
red fill (or dark gray fill) = gain of ≥80% of region,
green fill (or medium gray fill) = loss of ≥80% of region,
orange fill (light gray fill) = gain and loss within ≥80% of region,
red dot (dark gray dot) = gain of <80% of region,
green dot (medium gray dot) = loss of <80% of region.
Numbers in parentheses following each cell line name is the respective copy number used for gain/loss/normal status as derived from www.sanger.ac.uk/cgi-bin/genetics/CGP/cghviewer/CghHome.cgi.

For comparative purposes, the regions corresponding to those represented on the MatBA were designated as gain/loss/no change relative to the most frequent unaltered copy number for each cell line. This is exemplified by the dots in large regions such as for chr1: 142.4-153.3 and the filled boxes for chr2: 88-90 respectively. Such differences may represent larger CNVs that are different from expected due to the use of a different reference DNA and/or that CNVs were not removed from the published genomic profiles. For the cell lines, 697, SK-MM-2, and HT, overall good agreement between the expected and observed gains/losses was evident. Four other cell lines (EB2, L-428, Raji, KM-H2) also showed good correlation, when considering "normalization" using a fraction versus whole copy number for calling gain/loss for the publicly available data. For EB2, then normalization based on a copy number between 4 and 5 (rather than 4), for L-428 between 4 and 5 (rather than 4), for Raji between 1 and 2 (rather than 2), and for KM-H2 between 3 and 4 (rather than 3), yielded excellent correlation of gains/losses (not shown). Three cell lines exhibited discrepancies that could not be explained by ploidy issues. For two (Daudi and RPMI-8402), a large number of the changes were discrepant indicating the possibility that the cell lines are contaminated with another. For HDLM-2, less discrepancy was evident but enough to warrant confirmation of the changes by an independent procedure as recommended by the ACMG for array CGH-based assays. The discrepant changes are currently being evaluated by quantitative PCR.

Importantly, very little or no difference in aberration detection was noted between the two normalization procedures (whole array versus backbone alone). This is important since for mature B-cell neoplasms, a range of CNAs per specimen have been reported. In general, CNAs range from 0-30 per specimen, with DLBCL, MCL, and MM exhibiting greater genomic instability than FL, MZL, and CLL/SLL.

EXAMPLE 2

Microarray Assay for Chronic Lymphocytic Leukemia

Description of the Disease

Chronic lymphocytic leukemia (CLL) is one type of mature B-cell neoplasm (22). It occurs almost exclusively in adults with a median age at diagnosis of 65 to 68 years. It comprises approximately 10% of all adult hematologic malignancies, but 40% of leukemias in individuals over 65 years of age. In the US, approximately 15,000 new cases are diagnosed each year (23). At the present time, CLL is often detected in asymptomatic patients with an elevated lymphocyte count in a routine full blood count (24). Definitive diagnosis is based on a lymphocytosis and characteristic lymphocyte morphology and immunophenotype (24). Two major staging systems for the disease exist: Rai and Binet, which are useful for stratifying patients for clinical research studies, and have guided care and treatment approaches (24). The staging systems however, do not permit the identification of a significant proportion of patients with early stage disease that unexpectedly become active and refractory to treatment or with stable versus aggressive late stage disease. Thus, for a disease entity that presents predominantly in an aging population, accurate prognostication for treatment options is highly desirable.

Prognostication in CLL currently comprises the use of clinical features such as stage, expression of markers such as CD38 and ZAP-70 (by flow cytometry), IGHV mutation status (by PCR and sequencing), karyotype analysis, and fluorescence in situ hybridization (FISH) for the detection of gain or loss of four specific loci (13q, 11q, 17p, and 12) (13, 24). Cancer Genetics, Inc. (CGI) holds licensure for the performance of flow cytometry (CD38, with validations currently underway for ZAP-70), IGHV mutation status, karyotype analysis, and FISH for the four loci. In order to further assist in the diagnosis and prognosis of CLL, CGI has developed the mature B-cell neoplasm array (MatBA) array-based comparative genomic hybridization (MatBA-CLL Array-CGH) assay based on the identification of gain/loss of genomic material frequently observed in CLL and with prognostic value.

The Regions to be Tested and Alterations

Table 6 lists the genomic regions represented on the mature B-cell neoplasm array (MatBA) that was utilized. Those that were evaluated in the current test for gain/loss in CLL specimens by array-CGH according to the submitted SOPs are bolded. Additional regions were included on the array for the purposes of array normalization and potential utilization of the array for gain/loss evaluation in other mature B-cell neoplasms such as follicular lymphoma and diffuse large B-cell lymphoma.

Cytogenetic aberrations have been well documented to have prognostic significance in CLL (3, 25, 26). Such aberrations are routinely revealed by G-banding of metaphase chromosomes, and also by FISH for the abnormalities del(11q), del(13q), +12, and del(17p) (24). Deletions of 11q and 17p are associated with an unfavorable outcome while deletion of 13q as a sole abnormality, is associated with a favorable outcome (3, 4, 14). Multiple molecular genetic studies have narrowed the common regions of loss on 11q and 17p to include the ATM and TP53 genes. For 13q, array-CGH and molecular genetic studies have been revealed that two loci are targets of the deletion: RB1 and the microRNA loci (MIR-15A/16.1) (6). Array-CGH has revealed different patterns of deletion of these two loci, where approximately 60% of cases with a 13q loss, exhibit loss of the MIR locus and the remaining 40% display loss of both the MIR and RB1 loci, potentially with clinical significance (6). Of note, routine FISH does not permit distinction between CLL with the different patterns of loss at 13q. Other array-CGH studies have indicated the gain/loss of other genomic regions in CLL that potentially have clinical utility, and hence are represented and reported in the MatBA-CLL Array-CGH assay (1, 2, 8, 9, 12, 15, 17) (Table 7). Also listed in Table 7 are the minimum criteria used to score positive for a gain/loss of a specific region. When a target gene of the abnormality is known (MIR, RB1, TP53, ATM), the region is localized to that gene and usually small. For other regions, where target genes are much less well defined or only suggested, larger regions are used.

TABLE 6

Genomic Regions Represented on MatBA Used in Assay for CLL

| Region | Location (Mbp)* | Size (Mbp) |
| --- | --- | --- |
| 1p36.32-p36.23 | chr1: 1.5-9.4 | 7.9 |
| 1p21 | chr1: 94.0-107 | 13 |
| 1p13.2-p13.1 | chr1: 111.6-117.6 | 6 |
| 1q21 | chr1: 142.4-153.3 | 10.9 |
| 1q31 | chr1: 184.6-204.3 | 19.7 |
| 1q41-q44 | chr1: 236.5-244.5 | 8 |
| 2p25.3 | chr2: 2.4-4.1 | 1.7 |
| 2p16.1-p15 | chr2: 59.3-63.9 | 4.6 |
| 2p11.2-q11.2 | chr2: 88-90 | 2 |
| 2q13-2q14.1 | chr2: 113.6-114.2 | 0.6 |
| 2q24 | chr2: 154.6-169.5 | 14.9 |
| 3p22 | chr3: 32.1-42 | 9.9 |
| 3p14.1-p13 | chr3: 69.9-73.7 | 3.8 |
| 3q12.2-q12.3 | chr3: 102.0-103.2 | 1.2 |
| 3q21.2 | chr3: 126.4-126.7 | 0.3 |
| 3q22 | chr3: 131.5-140.4 | 8.9 |
| 3q26.1-q26.2 | chr3: 161.2-172.5 | 11.3 |
| 3q26.31 | chr3: 173-175 | 2 |
| 3q27 | chr3: 184.2-189.4 | 5.2 |
| 4p15 | chr4: 24.9-34.7 | 9.8 |
| 4q11-q12 | chr4: 52-56 | 4 |
| 4q24 | chr4: 102-104.8 | 2.8 |
| 4q34.3-q35 | chr4: 178.3-189.9 | 11.6 |
| 5p15 | chr5: 0-10 | 10 |
| 5q13.2-5q13.3 | chr5: 73-76 | 3 |
| 5q31.3 | chr5: 140-141 | 1 |
| 6p25 | chr6: 0-7 | 7 |
| 6p21.31-p21.2 | chr6: 35.7-37.7 | 2 |
| 6p21.1 | chr6: 41-43 | 2 |
| 6q12 | chr6: 66.9-67.2 | 0.3 |
| 6q16 | chr6: 92-104.8 | 12.8 |
| 6q21 | chr6: 108-110.5 | 2.5 |
| 6q22 | chr6: 113.9-130.4 | 16.5 |
| 6q23.3-q24 | chr6: 137.2-149.1 | 11.9 |
| 6q25 | chr6: 152.2-153.2 | 1 |
| 7p22 | chr7: 0-7.2 | 7.2 |
| 7p21.3-p21.2 | chr7: 12.9-14.6 | 1.7 |
| 7q31 | chr7: 107.2-126.9 | 19.7 |
| 8p23 | chr8: 0-12.7 | 12.7 |
| 8p21.3 | chr8: 18.7-23.2 | 4.5 |
| 8p12-p11.23 | chr8: 37.4-39.4 | 2 |
| 8q21.2 | chr8: 86.6-86.9 | 0.3 |
| 8q24.21 | chr8: 127.3-131.5 | 4.2 |
| 9p24.2-p24.1 | chr9: 4.0-6.0 | 2 |
| 9p21 | chr9: 19.9-32.8 | 12.9 |
| 9q22 | chr9: 89.6-101.6 | 12 |
| 9q33.2-q34.1 | chr9: 122-132 | 10 |
| 10p14 | chr10: 6.7-12.3 | 5.6 |
| 10p12.31-p12.2 | chr10: 21.6-24.1 | 2.5 |
| 10q23.2 | chr10: 87.9-89.8 | 1.9 |
| 11p13 | chr11: 33.0-34.5 | 1.5 |
| 11q13 | chr11: 63.1-76.7 | 13.6 |
| 11q22.1-q22.2 | chr11: 100.8-102.2 | 1.4 |
| 11q22.3-q23 | chr11: 106.7-120.7 | 14 |
| 11q25 | chr11: 132.5-134.5 | 2 |
| 12p13.1 | chr12: 12.6-14.8 | 2.2 |
| 12q13.1-q13.2 | chr12: 44.6-56.5 | 11.9 |
| 12q15 | chr12: 66-69.8 | 3.8 |
| 13q14 | chr13: 39.5-52.2 | 12.7 |
| 13q31 | chr13: 77.8-93.8 | 16 |
| 13q33-q34 | chr13: 100.5-114.1 | 13.6 |
| 14q12 | chr14: 23.5-32.5 | 9 |
| 14q32 | chr14: 90.1-105.1 | 15 |
| 15q21.1 | chr15: 44.0-45.5 | 1.5 |
| 15q23-q24 | chr15: 65-75 | 10 |
| 16p13.3 | chr16: 0-6.3 | 6.3 |
| 16p13.13 | chr16: 10.3-12.3 | 2 |
| 16p11.1-p11.2 | chr16: 27.6-38.2 | 10.6 |
| 16q24 | chr16: 83.6-88.8 | 5.2 |
| 17p13 | chr17: 0-11.2 | 11.2 |
| 17q22-q23.1 | chr17: 53-55 | 2 |
| 17q24.2-25.1 | chr17: 64.1-69.9 | 5.8 |
| 18p11 | chr18: 0-16.1 | 16.1 |
| 18q21 | chr18: 41.8-59.8 | 18 |
| 18q23 | chr18: 75.1-75.4 | 0.3 |
| 19p13.3-p13.2 | chr19: 0.2-11.2 | 11 |
| 19q13.33-q13.43 | chr19: 53.8-63.8 | 10 |
| 20q13 | chr20: 41.1-62.4 | 21.3 |

TABLE 6-continued

Genomic Regions Represented on MatBA Used in Assay for CLL

| Region | Location (Mbp)* | Size (Mbp) |
|---|---|---|
| 21q21 | chr21: 15.3-30.5 | 15.2 |
| 22q12 | chr22: 20-35.9 | 15.9 |

*Locations according to the March 2006 NCBI Build 36/hg18.

Cytogenetic aberrations have been well documented to have prognostic significance in CLL (3, 25, 26). Such aberrations are routinely revealed by G-banding of metaphase chromosomes, and also by FISH for the abnormalities del (11q), del(13q), +12, and del(17p) (24). Deletions of 11q and 17p are associated with an unfavorable outcome while deletion of 13q as a sole abnormality, is associated with a favorable outcome (3, 4, 14). Multiple molecular genetic studies have narrowed the common regions of loss on 11q and 17p to include the ATM and TP53 genes. For 13q, array-CGH and molecular genetic studies have been revealed that two loci are targets of the deletion: RB1 and the microRNA loci (MIR-15A/16.1) (6). Array-CGH has revealed different patterns of deletion of these two loci, where approximately 60% of cases with a 13q loss, exhibit loss of the MIR locus and the remaining 40% display loss of both the MIR and RB1 loci, potentially with clinical significance (6). Of note, routine FISH does not permit distinction between CLL with the different patterns of loss at 13q. Other array-CGH studies have indicated the gain/loss of other genomic regions in CLL that potentially have clinical utility, and hence are represented and reported in the MatBA-CLL Array-CGH assay (1, 2, 8, 9, 12, 15, 17) (Table 7). Also listed in Table 7 are the minimum criteria used to score positive for a gain/loss of a specific region. When a target gene of the abnormality is known (MIR, RB1, TP53, ATM), the region is localized to that gene and usually small. For other regions, where target genes are much less well defined or only suggested, larger regions are used.

TABLE 7

Minimum Criteria for Gain/Loss of Chromosomal Regions

| Aberration | Criteria |
|---|---|
| Loss of 8p (8p23.3-p21.3) | >90% of chr8: 0-12.7, 18.7-23.2 |
| Loss of 11q (ATM) | >90% of chr11: 106.7-109.7 |
| Loss of 13q (MIR) | >70% of chr13: 49.5-50 |
| Loss of 13q (RB1) | >33% of chr13: 47.5-49 |
| Loss of 17p (TP53) | >50% of chr17: 6.0-9.0 |
| Gain of 2p (2p25.3-p15) | >90% of chr2: 2.4-4.1, 59.3-63.9 |
| Gain of 3q (3q26.31-q27.3) | >90% of chr3: 173-175, 184.2-189.4 |
| Gain of 8q (8q24.21) | >90% of chr8: 127.3-131.5 |
| Gain of 12 (12p13.1-q15) | >90% of chr12: 12.6-14.8, 44.6-56.5, 66-69.8 |

For each of the reportable regions in MatBA-CLL array-CGH, secondary confirmation of the gain/loss is performed by quantitative PCR using the following list of representative genomic loci (Table 8). When known, copy number assays for the proposed target gene were utilized. Table 3 also lists the two reference genes, mapping to regions frequently unaltered in CLL.

TABLE 8

Representative Genomic Loci

| Aberration | Gene | Copy Number Assay |
|---|---|---|
| Loss of 8p | GATA4 | Hs01297945_cn |
|  | TNFRSF10B | Hs00098983_cn |
| Loss of 11q | ATM* | Hs02355120_cn |
| Loss of 13q | DLEU2^ | Hs03846573_cn |
| Loss of 13q | RB1* | Hs01344097_cn |
| Loss of 17p | TP53* | Hs05506931_cn |
| Gain of 2p | REL | Hs00231626_cn |
| Gain of 3q | BCL6 | Hs02145887_cn |
| Gain of 8q | MYC | Hs01764918_cn |
| Gain of 12 | MDM2 | Hs00738157_cn |
| Control | TERT | Cat#4403316 |
| Control | RAG2 | Hs00705088_cn |

*Reported target gene.
^MIR-15A/16.1 is within DLEU2 and the copy number assay selected is immediately centromeric to MIR-15A/16.1.

Array comparative genomic hybridization (CGH) involves the simultaneous hybridization of differentially labeled test and reference DNAs to a microarray (BAC or oligonucleotide-based) representative of the entire genome or parts thereof. In most applications, test DNA is labeled with Cy5-dUTP (red) and reference DNA is labeled with Cy3-dUTP (green). Following hybridization and scanning, BAC/oligonucleotide probes exhibiting increased red fluorescent signal over green is reflective of increased copy number of the sequence in the test DNA relative to the reference DNA (gain or amplification), increased green signal of decreased copy number in test DNA relative to reference DNA (loss), and yellow of no copy number change in the test DNA relative to the reference DNA. In MatBA array-CGH, the oligonucleotide-based microarray is designed by CGI (using eArray by Agilent Technologies) and manufactured by Agilent. MatBA has 80 regions of the human genome represented at an average resolution of 35 kbp (see Table 6) where all 17,348 oligonucleotides were from the Agilent library. It also contains a "backbone" of 3,100 oligonucleotides, provided by Agilent, that cover the entire human genome at an average resolution of 1,000 kbp. All oligonucleotide probes are represented in duplicate, in keeping with the guidelines established by the American Board of Medical Genetics (ABMG). In addition, 301 probes (each printed five times) are included in the array design to permit the assessment of reproducibility of each hybridization. With the printing of each array Agilent also includes oligonucleotides for alignment purposes, etc (2,118). This array was designed to permit use of the 4×44K format where four arrays per glass slide are hybridized at one time. Thus each array has 2,118 Agilent control, 1,505 reproducibility control, 6,200 backbone, and 34,696 selected region oligonucleotides (total of 44,519).

In MatBA-CLL array-CGH, test DNA comprises genomic DNA extracted from mononuclear cells enriched from blood or bone marrow of CLL patients. Reference DNA comprises an equimixture of commercially available male and female DNA (MF DNA, Promega). One (1) ug of each DNA is digested with the restriction enzymes RsaI and AluI, and then labeled with the respective fluor using Klenow. Following removal of unincorporated nucleotides, the differentially labeled DNAs are combined, and submitted to hybridization. Following a series of washes, the slide is dipped in a Stabilization and Drying reagent (Agilent) to reduce the effects of ozone on Cy3 fluorescence, and is then scanned in an Agilent Microarray scanner. The detected fluorescent signal intensities for each arrayed oligonucleotide are extracted using Feature Extraction Software (Agilent), and "aberrations" are detected using the Genomic Workbench 6.0 software (Agilent). In the latter case, gains and losses of genomic material in the test DNA relative to the reference DNA are identified based on the statistical significance of the difference in log ratios of the respective fluorescent signal intensities at consecutive oligonucleotides along the lengths of each chromosome compared to that of the entire array. Only those regions indicated above in Table 7 that exhibit gain or loss are reported in the current assay for CLL.

In keeping with the guidelines of the ABMG, gains/losses of genomic material as detected by array-CGH must be confirmed by an independent technology. Thus for each of the regions reported, a quantitative PCR (QPCR)-based assay has been established using, when known, the primers/probes for target genes of the respective genomic gain/loss loci. In all cases, Taqman-based QPCR is performed using copy-number assay probes/primers as selected from the Applied Biosystems Inc. (ABI) copy-number assay library. Two reference genes (TERT and RAG2) have been selected based on location at sites where few or no alterations are observed in CLL. In every QPCR assay, all amplifications are performed in duplicate, every plate contains no template controls for each gene assayed, every plate contains amplifications of the control genes for each DNA assayed, and every plate contains amplifications with two independently prepared reference DNAs (MF DNA).

Indications for Testing

Multiple FISH studies in CLL have revealed the prognostic significance of 17p loss (TP53) and 11q loss (ATM) with shorter time to first treatment (TTFT) and inferior survival, and of loss of 13q as a sole abnormality with longer TTFT and superior survival (3, 4, 14). These abnormalities are important biomarkers in CLL and are routinely assayed by FISH in clinical laboratories for both diagnostic and prognostic purposes (24). Most clinical laboratories also routinely assay for chromosome 12 gain, however the clinical significance of this aberration remains unclear. Array-CGH is a powerful technology wherein genomic gain/loss can be tested at higher resolution and potentially across the entire genomic complement. This then permits the assessment of diagnostic and prognostic genomic gains/losses at multiple loci simultaneously. Application of array-CGH to CLL specimen DNAs has revealed additional potential biomarkers, some with associations with clinical features and disease course (1, 2, 6-10, 12, 15, 17, 20). Table 9 summarizes the relevant studies (FISH- and array-based) that form the rationale for the performance of MatBA Array-CGH for diagnostic and prognostic value in CLL to assess genomic gain/loss at multiple loci. Of note, the references listed are not comprehensive but are representative.

TABLE 9

| Aberration | Findings | References |
|---|---|---|
| Loss of 8p | In 17p-CLL with shorter TTFT and OS | (1) |
| Loss of 11q | With shorter TTFT, OS, IGHV unmutated | (2-5) |

TABLE 9-continued

| Aberration | Findings | References |
|---|---|---|
| Loss of 13q | With longer TTFT and OS as a sole abnormality | (2, 3, 5) |
| Loss of 13q (MIR, RB1 vs MIR) | With advanced stage | (6) |
| Loss of 17p | With shorter TTFT, OS, IGHV unmutated | (2-4, 7) |
| Gain of 2p | With advanced stage and IGHV unmutated, in 17p-with shorter OS | (7, 8, 20, 21) |
| Gain of 3q | With 17p- | (7) |
| Gain of 8q | With 17p- | (7) |
| Gain of 12 | With longer TTFT and OS in some studies but not in others | (2, 3, 5) |

Accuracy of the detection of gains/losses by MatBA-CLL array-CGH was assessed using DNA extracted from seven cell lines with publicly available genomic copy number profiles (Affymetrix SNP6 oligonucleotide arrays, 946K copy number probes) (see, www.sanger.ac.uk/cgibin/genetics/CGP/cghviewer/CghHome.cgi). Cell lines with both few and many aberrations were selected. For comparative purposes, the regions corresponding to those represented on the MatBA and assessed during MatBA-CLL Array-CGH were designated as gain/loss/no change relative to the most frequent unaltered copy number for each cell line (Table 10). In Table 10, designated gains are shaded red (or dark gray) and designated losses shaded green (medium gray). Regions shaded in gold (or light gray) have both gains and losses and regions with partial gains/losses are hatched. Locations of changes of copy number within regions are noted. DNA from each cell line was submitted to MatBA-CLL Array-CGH with the exception that aberrations (gains/losses) were not detected and reported as for CLL. This is due to the fact that the cell lines are not CLL and thus do not show the typical gains/losses found in CLL as reported in the current assay. To this end, smaller aberrations (>1 Mbp) within reportable represented regions were also reported. The results are summarized in Table 10. All DNA digestions, labeling, and hybridizations were within acceptable ranges and all aberrations detected are given in the Cell Lines Aberrations file. For five cell lines, concordance was found for all regions. For EB2, discordance was found for 3q, 13q, and 17p. In the first case, a small deletion was detected when none was expected. QPCR was not performed to confirm/exclude the loss since the gene used for QPCR confirmation in the MatBA-CLL Array-CGH assay for the 3q region is BCL6 and it is located in the telomeric of the two regions that are reported as a combination. For 13q, the entire region was expected to exhibit a loss. By array-CGH, no loss was observed (Table 10) and follow-up QPCR confirmed this finding. For 17p, a 2 Mbp deletion

TABLE 10

| Represented Region | HT | | | Raji | | | EB2 | | | KMH2 | | | 697 | | | SKMM-2 | | | L-428 | | |
|---|---|---|---|---|---|---|---|---|---|---|---|---|---|---|---|---|---|---|---|---|---|
| | E | O | O | E | O | O | E | O | O | E | O | E | O | O | E | O | O | E | O | O |
| chr2: 2.4-4.1 | | | | | | | | | | | | | | | | | | | | | |
| chr2: 59.3-63.9 | | | | | | | | | | | | | | | | | | | | | |
| chr3: 173-175 | | | | | | | | | | | | | | | | | | | | | |
| chr3: 184.2-189.4 | | | | | | | | | | | | | | | | | | | | | |
| chr8: 0-12.7 | | | | | | | | | | | | | | | | | | | | | |
| chr8: 18.7-23.2 | | | | | | | | | | | | | | | | | | | | | |
| chr8: 127.3-131.5 | | | | | | | | | | | | | | | | | | | | | |
| chr11: 106.7-120.7 | | | | | | | | | | | | | | | | | | | | | |
| chr12: 12.6-14.8 | | | | | | | | | | | | | | | | | | | | | |
| chr12: 44.6-56.5 | | | | | | | | | | | | | | | | | | | | | |
| chr12: 66-69.8 | | | | | | | | | | | | | | | | | | | | | |
| chr13: 39.5-52.2 | | | | | | | | | | | | | | | | | | | | | |
| chr17: 0-11.2 | | | | | | | | | | | | | | | | | | | | | |

E = expected (Table 11),
O = observed (results for duplicate experiments are shown).

was not detected by array-CGH using MatBA and could be explained by highly recurrent CNVs often observed in this small genomic region as according to the Database of Genomic Variants (http://projects.tcag.ca/variation/). In L-428, two discrepancies were observed: a low level gain of 8p (one copy number gain) was identified as only a partial gain and a loss was identified on 2p (chr2: 2.4-4.1). These discordant results can be explained when considering the "normalization" to a whole copy number that was performed to designate regions as gain/loss from the publicly available copy number data. A fraction versus whole copy number for calling gain/loss is more appropriate in this case. For L-428 between 4 and 5 (rather than 4) would seem a better "normalization" copy number and explain the discrepancies. Of note, partial gains and losses and mixed gains/losses within regions were accurately detected by array-CGH using MatBA-CLL. Precision/reproducibility of array-CGH using MatBA was evaluated by independent repeat digestion, labeling, and hybridization of six cell lines (KMH2 was not repeated due to lack of DNA, Table 10). Only in one cell line was a discrepancy noted: L-428 for the region (chr2: 2.4-4.1). The discrepancy only involved a partial regional loss and already involved an alteration affected by ploidy and which in the current MatBA-CLL Array-CGH assay would not be apparent due to the stringent requirements for an aberration to be called positive (Table 5). The limit of detection of the MatBA-CLL Array-CGH was assessed by submitting to MatBA-CLL Array-CGH, dilutions of four cell line DNAs. Cell line DNA was diluted with placental

TABLE 11

| Represented Region | 697 100% | 697 40% | 697 30% | KMH2 100% | KMH2 40% | KMH2 30% | SKMM-2 100% | SKMM-2 40% | SKMM-2 30% | L-428 100% | L-428 40% | L-428 30% |
|---|---|---|---|---|---|---|---|---|---|---|---|---|
| chr2: 2.4-4.1 | | | | ■ | ▨ | | | | | ■ | | ▨ |
| chr2: 59.3-63.9 | | | | ■ | ■ | ▨ | | | | ■ | | ▨ |
| chr3: 173-175 | | | | | ▨ | | | | | | | |
| chr3: 184.2-189.4 | | | | | | | | | | | | |
| chr8: 0-12.7 | | | | ▨ | ▨ | | ■ | ▨ | | | | |
| chr8: 18.7-23.2 | | | | ■ | | | ■ | ▨ | ▨ | | | |
| chr8: 127.3-131.5 | ■ | ■ | ▨ | | | | ■ | ■ | ■ | ■ | ■ | ▨ |
| chr11: 106.7-120.7 | | | | ■ | ▨ | | ■ | ■ | ▨ | ▨ | ▨ | ▨ |
| chr12: 12.6-14.8 | | | | ■ | ▨ | ▨ | | | | ■ | ■ | |
| chr12: 44.6-56.5 | | | | ▨ | ▨ | ▨ | | | | ▨ | ▨ | ▨ |
| chr12: 66-69.8 | | | | | | | | | | ▨ | ▨ | ▨ |
| chr13: 39.5-52.2 | | | | ■ | | ▨ | ■ | ■ | ■ | ■ | ■ | ▨ |
| chr17: 0-11.2 | | | | ■ | ■ | ▨ | ■ | ■ | ■ | ■ | ■ | ▨ |

DNA from a normal individual (Plac) to achieve the respective percentages shown in Table 11 as well as 25% and 20%. A file of the aberrations detected in these cell line dilutions is provided (Cell Lines Aberrations). Table 11 shows the gains/losses observed for each cell line based on that observed for 100% cell line DNA. Across the four cell lines, aberrations were routinely observed at 40% dilution. Fewer were observed at 30% and these were predominantly gains where higher copy number increases are observed. For all cell lines, aberrations were not detected at lower dilutions (25% and 20%) with the exception of a partial high level gain of the 2p locus (chr2: 59.3-63.9) that was routinely detected down to 25% dilution, as expected based on the high copy number noted in Table 10 for a locus within this region. Overall, the limit of routine detection by MatBA-CLL Array-CGH assay is 30%-40%, consistent with other array-CGH studies.

TABLE 12

| Represented Region | QPCR Locus | 697* 100% | 697* 40% | 697* 30% | SKMM-2 100% | SKMM-2 40% | SKMM-2 30% | L-428 100% | L-428 40% | L-428 30% |
|---|---|---|---|---|---|---|---|---|---|---|
| chr2: 59.3-63.9 | | | | | | | | ■ | | ▨ |
| | REL | | | | | | | P | P | P |
| chr8: 0-12.7 | | | | | ■ | | ▨ | | | |
| | GATA4 | | | | P | P | N | | | |
| chr8: 18.7-23.2 | | | | | ■ | | | ▨ | | |
| | TNFRSF10B | | | | P | P | N | | | |
| chr8: 127.3-131.5 | | | ■ | ▨ | ■ | ■ | ■ | ■ | ■ | ■ |
| | MYC | P | P | P | P | P | P | P | P | N |
| chr11: 106.7-120.7 | | | | | ■ | | ▨ | | | |
| | ATM | | | | P | P | N | P | P | P |
| chr12: 66-69.8 | | | | | | | | ▨ | | |
| | MDM2 | | | | | | | | P | N |
| chr13: 39.5-52.2 | | | | | ■ | | ▨ | ■ | | |
| | MIR/RB1 | | | | P | P | P | P | P | P |
| chr17: 0-11.2 | | | | | ■ | | | ■ | | ▨ |
| | TP53 | | | | P | P | N | P | N | N |

*P = positive by QPCR for the change, N = negative for the change.

The limit of detection of the QPCR was assessed by submitting three of the cell line DNA dilutions to QPCR. QPCR was not performed for KMH2 due to lack of additional DNA. The results of the QPCR are summarized in Table 16. QPCR was not performed for regions where partial gains/losses were observed in 100% cell line DNA. Of note, partial gain/loss of a reportable region is not reported in MatBA-CLL Array-CGH and is only used in the current validations due to the availability of non-CLL cell lines with appropriate gains/losses within the reportable regions. All expected gains/losses were confirmed by QPCR with the exception of partial gains/losses where the partial gain/loss was not located at site of the tested gene, and of TP53 loss in L-428 (40%) where the aberration was only detected at a low log ratio and only at the lowest stringency. QPCR using the criteria in the SOP (MS41), yielded a comparable sensitivity to that of MatBA Array-CGH. It is generally accepted that QPCR is a highly sensitive technique for detecting changes in analyte levels. It is important to note, that in the current application only small changes in "level" of an analyte are being evaluated (often gain or loss of a single copy number of a locus), as compared to for example large fold changes observed in gene expression levels. Higher level gain (such as amplification) was detected at high sensitivity as noted in Table 12.

REFERENCES

1. Forconi F, Rinaldi A, Kwee I, et al. Genome-wide DNA analysis identifies recurrent imbalances predicting outcome in chronic lymphocytic leukaemia with 17p deletion. Br J Haematol 2008; 143(4):532-6.
2. Gunnarsson R, Isaksson A, Mansouri M, et al. Large but not small copy-number alterations correlate to high-risk genomic aberrations and survival in chronic lymphocytic leukemia: a high-resolution genomic screening of newly diagnosed patients. Leukemia; 24(1):211-5.
3. Dohner H, Stilgenbauer S, Benner A, et al. Genomic aberrations and survival in chronic lymphocytic leukemia. N Engl J Med 2000; 343(26):1910-6.
4. Haferlach C, Dicker F, Schnittger S, Kern W, Haferlach T. Comprehensive genetic characterization of CLL: a study on 506 cases analysed with chromosome banding analysis, interphase FISH, IgV(H) status and immunophenotyping. Leukemia 2007; 21(12):2442-51.
5. Zenz T, Dohner H, Stilgenbauer S. Genetics and risk-stratified approach to therapy in chronic lymphocytic leukemia. Best Pract Res Clin Haematol 2007; 20(3):439-53.
6. Ouillette P, Erba H, Kujawski L, Kaminski M, Shedden K, Malek S N. Integrated genomic profiling of chronic lymphocytic leukemia identifies subtypes of deletion 13q14. Cancer Res 2008; 68(4):1012-21.
7. Rudenko H C, Else M, Dearden C, et al. Characterising the TP53-deleted subgroup of chronic lymphocytic leukemia: an analysis of additional cytogenetic abnormalities detected by interphase fluorescence in situ hybridisation and array-based comparative genomic hybridisation. Leuk Lymphoma 2008; 49(10):1879-86.
8. Chapiro E, Leporrier N, Radford-Weiss I, et al. Gain of the short arm of chromosome 2 (2p) is a frequent recurring chromosome aberration in untreated chronic lymphocytic leukemia (CLL) at advanced stages. Leuk Res; 34(1):63-8.
9. Hagenkord J M, Monzon F A, Kash S F, Lilleberg S, Xie Q, Kant J A. Array-based karyotyping for prognostic assessment in chronic lymphocytic leukemia: performance comparison of Affymetrix 10K2.0, 250K Nsp, and SNP6.0 arrays. J Mol Diagn; 12(2):184-96.
10. Ouillette P, Fossum S, Parkin B, et al. Aggressive chronic lymphocytic leukemia with elevated genomic complexity is associated with multiple gene defects in the response to DNA double-strand breaks. Clin Cancer Res; 16(3):835-47.
11. Van Dyke D L, Shanafelt T D, Call T G, et al. A comprehensive evaluation of the prognostic significance of 13q deletions in patients with B-chronic lymphocytic leukaemia. Br J Haematol; 148(4):544-50.
12. Schwaenen C, Nessling M, Wessendorf S, et al. Automated array-based genomic profiling in chronic lymphocytic leukemia: development of a clinical tool and discovery of recurrent genomic alterations. Proc Natl Acad Sci USA 2004; 101(4):1039-44.
13. Shanafelt T D, Geyer S M, Kay N E. Prognosis at diagnosis: integrating molecular biologic insights, into clinical practice for patients with CLL. Blood 2004; 103(4):1202-10.
14. Shanafelt T D, Witzig T E, Fink S R, et al. Prospective evaluation of clonal evolution during long-term follow-up of patients with untreated early-stage chronic lymphocytic leukemia. J Clin Oncol 2006; 24(28):4634-41. CGI—Confidential/Do Not Distribute Page 9
15. Gunn S R, Mohammed M S, Gorre M E, et al. Whole-genome scanning by array comparative genomic hybridization as a clinical tool for risk assessment in chronic lymphocytic leukemia. J Mol Diagn 2008; 10(5):442-51.
16. Patel A, Kang S H, Lennon P A, et al. Validation of a targeted DNA microarray for the clinical evaluation of recurrent abnormalities in chronic lymphocytic leukemia. Am J Hematol 2008; 83(7):540-6.
17. Grubor V, Krasnitz A, Troge J E, et al. Novel genomic alterations and clonal evolution in chronic lymphocytic leukemia revealed by representational oligonucleotide microarray analysis (ROMA). Blood 2009; 113(6):1294-303.
18. Gunn S R, Bolla A R, Barron L L, et al. Array CGH analysis of chronic lymphocytic leukemia reveals frequent cryptic monoallelic and biallelic deletions of chromosome 22q11 that include the PRAME gene. Leuk Res 2009; 33(9):1276-81.
19. Schwaenen C, Viardot A, Berger H, et al. Microarray-based genomic profiling reveals novel genomic aberrations in follicular lymphoma which associate with patient survival and gene expression status. Genes Chromosomes Cancer 2009; 48(1):39-54.
20. Pfeifer D, Pantic M, Skatulla I, et al. Genome-wide analysis of DNA copy number changes and LOH in CLL using high-density SNP arrays. Blood 2007; 109(3):1202-10.
21. Jarosova M, Urbankova H, Plachy R, et al. Gain of chromosome 2p in chronic lymphocytic leukemia: significant heterogeneity and a new recurrent dicentric rearrangement. Leuk Lymphoma; 51(2):304-13.
22. Chiorazzi N, Rai K R, Ferrarini M. Chronic lymphocytic leukemia. N Engl J Med 2005; 352(8):804-15.
23. Jemal A, Siegel R, Ward E, Hao Y, Xu J, Thun M J. Cancer statistics, 2009. CA Cancer J Clin 2009; 59(4):225-49.
24. Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood 2008; 111(12):5446-56.
25. Mossafa H, Huret, J L. Chronic lymphocytic leukemia (CLL). Atlas Genet Cytogenet Oncol Haematol 1997.
26. Reddy K. Chronic lymphocytic leukemia (CLL). Atals Genet Cytogenet Oncol Haemotol 2005.
27. Oscier D G, Thompsett A, Zhu D, Stevenson F K. Differential rates of somatic hypermutation in V(H) genes among subsets of chronic lymphocytic leukemia defined by chromosomal abnormalities. Blood 1997; 89(11):4153-60.
28. Fais F, Ghiotto F, Hashimoto S, et al. Chronic lymphocytic leukemia B cells express restricted sets of mutated and unmutated antigen receptors. J Clin Invest 1998; 102 (8):1515-25.
29. Damle R N, Wasil T, Fais F, et al. Ig V gene mutation status and CD38 expression as novel prognostic indicators in chronic lymphocytic leukemia. Blood 1999; 94(6):1840-7.
30. Hamblin T J, Davis Z, Gardiner A, Oscier D G, Stevenson F K. Unmutated Ig V(H) genes are associated with a more aggressive form of chronic lymphocytic leukemia. Blood 1999; 94(6):1848-54.
31. Hamblin T J. Prognostic markers in chronic lymphocytic leukaemia. Best Pract Res Clin Haematol 2007; 20(3):455-68.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of detecting the type of mature B-cell neoplasm present in a sample, said method comprising:
    (a) providing a microarray, said microarray comprising a substrate with a plurality of distinct genomic regions and a backbone probe set that covers the entire human chromosomal complement arrayed thereon, wherein the backbone probe set covers the entire chromosomal complement at a resolution with an average density of approximately 1 Mbp, wherein each of the distinct genomic regions is individually capable of hybridizing to material present in said sample, wherein the genomic regions arrayed on the substrate are regions, wherein an alteration therein is correlated to one or more types of mature B-cell neoplasm, wherein the plurality of distinct genomic regions is all of the human genomic regions set forth in Table 6 and wherein the distinct genomic regions are between 0.3 to 21.3 Mbp in size and are represented on the microarray at a resolution with an average density of about 35 kbp;
    (b) providing the sample with labeled sample genetic material therein and labeled reference genetic material;
    (c) hybridizing the labeled sample genetic material and the labeled reference genetic material with the genomic regions and the backbone probe set arrayed on the substrate;
    (d) analyzing the hybridization pattern of the labeled sample genetic material to the genomic regions relative to the hybridization pattern of the reference genetic material to the genomic regions to detect the presence of alterations in the genetic material from the sample; and
    (e) correlating any detected alterations to the type of mature B-cell neoplasm associated with the alteration.

2. The method of claim 1, wherein the mature B-cell neoplasm is selected from the group consisting of Hodgkin's lymphoma, non-Hodgkin's lymphoma (NHL), and multiple myeloma.

3. The method of claim 1, wherein the mature B-cell neoplasm is CLL.

4. The method of claim 3, wherein step (e) comprises correlating gains or losses at 2p25.3, 2p16.1-p15, 3q26.31, 3q27, 8p23, 8p21.3, 8q24.21, 11q22.3-q23, 12p13.1, 12q13.1-q13.2, 12q15, 13q14, and 17p13 to CLL.

5. The method of claim 1, further comprising confirming all of the aberrations set forth in Table 8 by a copy number assay.

6. The method of claim 5, wherein the copy number assay comprises determining the copy number of: GATA4 and TNFRSF10B for loss of 8p; ATM for loss of 11q; DLEU2 and RB1 for loss of 13q; TP53 for loss of 17p; REL for gain of 2p; BCL6 for gain of 3q; MYC for gain of 8q; and MDM2 for gain of 12.

7. The method of claim 1, wherein the alteration is the gain or loss of the genomic region or part thereof.

8. The method of claim 1, wherein labeled sample genetic material and the labeled reference genetic material are hybridized with the genomic regions arrayed on the substrate at the same time.

9. The method of claim 8, wherein the labeled genetic material comprises a first label and the labeled reference nucleic acid comprises a second label, wherein the first and second labels are non-identical and can be detected simultaneously when hybridized to at least one genomic region on the substrate.

10. The method of claim 9, wherein step (d) comprises acquiring an image of a microarray including a target spot; processing the image to correct for background noise and chip misalignment; analyzing the image to detect target spots; analyzing the image to identify the target patch, editing debris and correcting for ratio bias; detecting number variation in the target spot by an objective statistical analysis, wherein the sample genetic material and the reference genetic material form the target spot by the hybridizing; measuring a fluorescent signal intensity of the target spot from the sample genetic material and the reference genetic material; obtaining an image; and cross-correlating the image to the image of the microarray.

11. The microarray of claim 1, wherein the backbone probe set excludes regions of known copy number variation.

* * * * *

UNITED STATES PATENT AND TRADEMARK OFFICE
CERTIFICATE OF CORRECTION

| | | |
|---|---|---|
| PATENT NO. | : 8,580,713 B2 | |
| APPLICATION NO. | : 13/475034 | |
| DATED | : November 12, 2013 | |
| INVENTOR(S) | : Chaganti et al. | |

It is certified that error appears in the above-identified patent and that said Letters Patent is hereby corrected as shown below:

In the Claims

Column 38 (Claim 11), line 17, delete "microarray" and insert --method-- therefor.

Signed and Sealed this
Seventh Day of January, 2014

Margaret A. Focarino
*Commissioner for Patents of the United States Patent and Trademark Office*